i511559B2

United States Patent
Clifton et al.

(10) Patent No.: US 11,571,559 B2
(45) Date of Patent: *Feb. 7, 2023

(54) SUPPORT STRUCTURES FOR INTRAVASCULAR BLOOD PUMPS

(71) Applicant: PROCYRION, INC., Houston, TX (US)

(72) Inventors: William Clifton, Houston, TX (US); Ronald G. Earles, Houston, TX (US); Benjamin Hertzog, Houston, TX (US); Jason J. Heuring, Houston, TX (US); Christopher A. Durst, Houston, TX (US); Omar Benavides, Houston, TX (US); Eric S. Fain, Menlo Park, CA (US)

(73) Assignee: PROCYRION, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/833,706

(22) Filed: Jun. 6, 2022

(65) Prior Publication Data
US 2022/0296880 A1 Sep. 22, 2022

Related U.S. Application Data

(63) Continuation of application No. 17/535,330, filed on Nov. 24, 2021, now Pat. No. 11,351,359, which is a (Continued)

(51) Int. Cl.
*A61M 60/825* (2021.01)
*F04D 7/00* (2006.01)
(Continued)

(52) U.S. Cl.
CPC ........ *A61M 60/865* (2021.01); *A61M 60/139* (2021.01); *A61M 60/237* (2021.01); *A61M 60/861* (2021.01)

(58) Field of Classification Search
CPC .............. A61M 60/139; A61M 60/585; A61M 60/226; A61M 60/419; A61M 60/221;
(Continued)

(56) References Cited

U.S. PATENT DOCUMENTS 2,896,926 A 7/1959 Chapman
2,935,068 A 5/1960 Donaldson
(Continued)

FOREIGN PATENT DOCUMENTS

EP 2388029 11/2011
IT 31466 12/2010
(Continued)

OTHER PUBLICATIONS

Demirsoy, Ergun et al., Grafting the restenosed coronary artery after removal of multiple failed stents by endarterectomy, Texas Heart Institute Journal, Endarterectomy of Multiple Stents Before Grafts, 2006, vol. 33, No. 2, pp. 262-263.
(Continued)

*Primary Examiner* — Erin M Piateski
(74) *Attorney, Agent, or Firm* — Knobbe, Martens, Olson & Bear LLP

(57) ABSTRACT

An improved system for supporting (e.g., localization and/or positioning of) intravascular devices discussed herein provides for example a multi-element arrangement. A set of struts optionally projects from the intravascular device and contacts the vessel walls. The localization and positioning of the pump may be provided by the struts and/or by use of a tether opposing a propulsive force to ensure localization.

14 Claims, 15 Drawing Sheets

Related U.S. Application Data continuation of application No. PCT/US2020/064489, filed on Dec. 11, 2020, which is a continuation-in-part of application No. PCT/US2020/062928, filed on Dec. 2, 2020.

(60) Provisional application No. 62/947,940, filed on Dec. 13, 2019.

(51) Int. Cl.

| | |
|---|---|
| *F04D 29/043* | (2006.01) |
| *F04D 13/06* | (2006.01) |
| *F04D 29/52* | (2006.01) |
| *A61M 60/226* | (2021.01) |
| *A61M 60/419* | (2021.01) |
| *A61M 60/585* | (2021.01) |
| *A61M 60/13* | (2021.01) |
| *A61M 60/865* | (2021.01) |
| *A61M 60/237* | (2021.01) |
| *A61M 60/139* | (2021.01) |
| *A61M 60/861* | (2021.01) |

(58) Field of Classification Search
CPC .. A61M 60/824; A61M 60/13; A61M 60/825; A61M 60/808; A61M 60/82; F04D 7/00; F04D 13/026; F04D 13/06; F04D 29/043; F04D 29/0467; F04D 29/181; F04D 29/528
USPC .......................................................... 600/16
See application file for complete search history.

(56) References Cited

U.S. PATENT DOCUMENTS

| | | |
|---|---|---|
| 3,455,540 A | 7/1969 | Marcmann |
| 3,510,229 A | 5/1970 | Smith |
| 3,620,584 A | 11/1971 | Rosenweig |
| 3,812,812 A | 5/1974 | Hurwitz |
| 4,127,384 A | 11/1978 | Fahlvik et al. |
| 4,141,603 A | 2/1979 | Remmers et al. |
| 4,304,524 A | 12/1981 | Coxon |
| 4,407,508 A | 10/1983 | Raj et al. |
| 4,613,329 A | 9/1986 | Bodicky |
| 4,625,712 A | 12/1986 | Wampler |
| 4,643,641 A | 2/1987 | Clausen et al. |
| 4,753,221 A | 6/1988 | Kensey et al. |
| 4,846,152 A | 7/1989 | Wampler et al. |
| 4,900,227 A | 2/1990 | Trouplin |
| 4,919,647 A | 4/1990 | Nash |
| 4,944,722 A | 7/1990 | Carriker et al. |
| 4,969,865 A | 11/1990 | Hwang et al. |
| 4,994,017 A | 2/1991 | Yozu |
| 5,007,513 A | 4/1991 | Carlson |
| 5,147,388 A | 9/1992 | Yamazaki |
| 5,201,679 A | 4/1993 | Velte, Jr. et al. |
| 5,207,695 A | 5/1993 | Trout, III |
| 5,211,546 A | 5/1993 | Isaacson et al. |
| 5,368,438 A | 11/1994 | Raible |
| 5,393,197 A | 2/1995 | Lemont et al. |
| 5,405,383 A | 4/1995 | Barr |
| 5,490,763 A | 2/1996 | Abrams et al. |
| 5,527,159 A | 6/1996 | Bozeman, Jr. et al. |
| 5,534,287 A | 7/1996 | Lukic |
| 5,588,812 A | 12/1996 | Taylor et al. |
| 5,613,935 A | 3/1997 | Jarvik |
| 5,660,397 A | 8/1997 | Holtkamp |
| 5,686,045 A | 11/1997 | Carter |
| 5,722,930 A | 3/1998 | Larson, Jr. et al. |
| 5,725,570 A | 3/1998 | Heath |
| 5,749,855 A | 5/1998 | Reitan |
| 5,824,070 A | 10/1998 | Jarvik |
| 5,827,171 A | 10/1998 | Dobak, III et al. |
| 5,911,685 A | 6/1999 | Siess et al. |
| 5,921,913 A | 7/1999 | Seiss |
| 5,947,703 A | 9/1999 | Nojiri et al. |
| 5,951,263 A | 9/1999 | Taylor et al. |
| 5,964,694 A | 10/1999 | Siess et al. |
| 6,007,478 A | 12/1999 | Siess et al. |
| 6,136,025 A | 10/2000 | Barbut et al. |
| 6,227,797 B1 | 5/2001 | Watterson et al. |
| 6,245,026 B1 | 6/2001 | Campbell et al. |
| 6,253,769 B1 | 7/2001 | LaFontaine et al. |
| 6,302,910 B1 | 10/2001 | Yamazaki et al. |
| 6,517,315 B2 | 2/2003 | Belady |
| 6,533,716 B1 | 3/2003 | Schmitz-Rode et al. |
| 6,547,519 B2 | 4/2003 | deBlanc et al. |
| 6,585,756 B1 | 7/2003 | Strecker |
| 6,609,883 B2 | 8/2003 | Woodard et al. |
| 6,616,323 B2 | 9/2003 | McGill |
| 6,638,011 B2 | 10/2003 | Woodard et al. |
| 6,645,241 B1 | 11/2003 | Strecker |
| 6,660,014 B2 | 12/2003 | Demarais et al. |
| 6,716,189 B1 | 4/2004 | Jarvik et al. |
| 6,749,598 B1 | 6/2004 | Keren et al. |
| 6,860,713 B2 | 3/2005 | Hoover |
| 6,866,805 B2 | 3/2005 | Hong et al. |
| 6,887,215 B2 | 5/2005 | McWeeney |
| 6,972,956 B2 | 12/2005 | Franz et al. |
| 7,011,620 B1 | 3/2006 | Siess |
| 7,125,376 B2 | 10/2006 | Viole et al. |
| 7,189,260 B2 | 3/2007 | Harvath et al. |
| 7,374,531 B1 | 5/2008 | Kantrowitz |
| 7,381,034 B2 | 6/2008 | Shishido |
| 7,393,181 B2 | 7/2008 | McBride et al. |
| 7,396,327 B2 | 7/2008 | Morello |
| 7,473,220 B2 | 1/2009 | Francese et al. |
| 7,534,258 B2 | 5/2009 | Gomez et al. |
| 7,682,673 B2 | 3/2010 | Houston et al. |
| 7,758,806 B2 | 7/2010 | Zhao |
| 7,762,941 B2 | 7/2010 | Jarvik |
| 7,841,976 B2 | 11/2010 | McBride et al. |
| 7,878,967 B1 | 2/2011 | Khanal |
| 7,914,436 B1 | 3/2011 | Kung |
| 7,993,259 B2 | 8/2011 | Kang et al. |
| 7,998,054 B2 | 8/2011 | Bolling |
| 8,012,079 B2 * | 9/2011 | Delgado, III ........ A61M 60/237 623/1.36 |
| 8,088,059 B2 | 1/2012 | Jarvik |
| 8,177,703 B2 | 5/2012 | Smith et al. |
| 8,403,824 B2 | 3/2013 | Foster |
| 8,579,858 B2 | 11/2013 | Reitan et al. |
| 8,591,393 B2 | 11/2013 | Walters et al. |
| 8,597,170 B2 | 12/2013 | Walters et al. |
| 8,641,594 B2 | 2/2014 | LaRose et al. |
| 8,727,959 B2 | 5/2014 | Reitan et al. |
| 8,731,664 B2 | 5/2014 | Foster et al. |
| 8,734,508 B2 | 5/2014 | Hastings et al. |
| 8,777,832 B1 | 7/2014 | Wang et al. |
| 8,992,407 B2 | 3/2015 | Smith et al. |
| 9,138,517 B2 | 9/2015 | Garrigue |
| 9,138,518 B2 | 9/2015 | Campbell et al. |
| 9,144,638 B2 | 9/2015 | Zimmermann et al. |
| 9,162,018 B2 | 10/2015 | Foster |
| 9,199,020 B2 | 12/2015 | Siess |
| 9,265,870 B2 | 2/2016 | Reichenbach et al. |
| 9,415,147 B2 | 8/2016 | Akkerman et al. |
| 9,433,713 B2 | 9/2016 | Corbett et al. |
| 9,486,566 B2 | 11/2016 | Siess |
| 9,533,084 B2 | 1/2017 | Siess et al. |
| 9,572,915 B2 | 2/2017 | Heuring et al. |
| 9,616,159 B2 | 4/2017 | Anderson et al. |
| 9,744,281 B2 | 8/2017 | Siegenthaler |
| 9,759,222 B2 | 9/2017 | Zimmermann et al. |
| 9,777,732 B2 | 10/2017 | LaRose et al. |
| 9,907,890 B2 | 3/2018 | Muller |
| 9,919,089 B2 | 3/2018 | Garrigue |
| 10,039,873 B2 | 8/2018 | Siegenthaler |
| 10,111,994 B2 | 10/2018 | Wu et al. |
| 10,195,324 B2 | 2/2019 | Foster |
| 10,201,645 B2 | 2/2019 | Muller |
| 10,413,648 B2 | 9/2019 | Delgado, III |
| 10,443,738 B2 | 10/2019 | Durst et al. |

(56) References Cited

U.S. PATENT DOCUMENTS

| | | |
|---|---|---|
| 10,722,627 B1 | 7/2020 | Obeid et al. |
| 11,235,138 B2 | 2/2022 | Gross-Hardt et al. |
| 11,241,569 B2 | 2/2022 | Delgado, III |
| 11,324,940 B2 | 5/2022 | Earles et al. |
| 11,351,359 B2 | 6/2022 | Clifton et al. |
| 2002/0018713 A1 | 2/2002 | Woodard et al. |
| 2002/0151761 A1 | 10/2002 | Viole et al. |
| 2002/0169413 A1 | 11/2002 | Keren et al. |
| 2003/0105383 A1 | 6/2003 | Barbut et al. |
| 2003/0144574 A1 | 7/2003 | Heilman et al. |
| 2003/0176912 A1 | 9/2003 | Chuter et al. |
| 2003/0233143 A1 | 12/2003 | Gharib et al. |
| 2004/0044266 A1 | 3/2004 | Siess et al. |
| 2004/0046466 A1 | 3/2004 | Siess et al. |
| 2005/0131271 A1 | 6/2005 | Benkowski et al. |
| 2005/0220636 A1 | 10/2005 | Henein et al. |
| 2006/0036127 A1 | 2/2006 | Delgado, III |
| 2006/0062672 A1 | 3/2006 | McBride et al. |
| 2006/0155159 A1 | 7/2006 | Melvin |
| 2007/0004959 A1 | 1/2007 | Carrier et al. |
| 2007/0156006 A1 | 7/2007 | Smith et al. |
| 2008/0103591 A1 | 5/2008 | Siess |
| 2009/0093764 A1 | 4/2009 | Pfeffer et al. |
| 2009/0149950 A1 | 6/2009 | Wampler |
| 2010/0174131 A1 | 7/2010 | Foster et al. |
| 2010/0249489 A1 | 9/2010 | Jarvik |
| 2011/0106115 A1 | 5/2011 | Haselby et al. |
| 2011/0152999 A1 | 6/2011 | Hastings et al. |
| 2011/0160844 A1 | 6/2011 | Haselby et al. |
| 2011/0238172 A1 | 9/2011 | Akdis |
| 2011/0318204 A1 | 12/2011 | Omori |
| 2012/0029265 A1 | 2/2012 | LaRose et al. |
| 2012/0041255 A1 | 2/2012 | Delgado, III |
| 2012/0134832 A1 | 5/2012 | Wu |
| 2012/0172654 A1 | 7/2012 | Bates |
| 2013/0053623 A1 | 2/2013 | Evans et al. |
| 2013/0303831 A1 | 11/2013 | Evans |
| 2014/0128659 A1 | 5/2014 | Heuring et al. |
| 2014/0200664 A1 | 7/2014 | Akkerman et al. |
| 2014/0275722 A1 | 9/2014 | Zimmermann et al. |
| 2014/0275726 A1 | 9/2014 | Zeng |
| 2015/0258260 A1 | 9/2015 | Tuseth |
| 2015/0285258 A1 | 10/2015 | Foster |
| 2016/0045652 A1 | 2/2016 | Cornen |
| 2016/0045653 A1 | 2/2016 | Siess |
| 2016/0346450 A1 | 12/2016 | Akkerman et al. |
| 2017/0043074 A1 | 2/2017 | Siess |
| 2017/0087288 A1 | 3/2017 | Grob-Hardt et al. |
| 2017/0197019 A1 | 7/2017 | Tuseth et al. |
| 2017/0216507 A1 | 8/2017 | Kushwaha et al. |
| 2017/0296720 A1 | 10/2017 | Taskin et al. |
| 2017/0340789 A1 | 11/2017 | Bonde et al. |
| 2018/0010608 A1 | 1/2018 | LaRose et al. |
| 2018/0050139 A1 | 2/2018 | Siess et al. |
| 2018/0050140 A1 | 2/2018 | Siess et al. |
| 2018/0050142 A1 | 2/2018 | Siess et al. |
| 2018/0064861 A1 | 3/2018 | Dur et al. |
| 2018/0154057 A1 | 6/2018 | Garrigue |
| 2018/0169412 A1 | 6/2018 | Barry |
| 2018/0193543 A1 | 7/2018 | Sun |
| 2018/0228953 A1 | 8/2018 | Siess et al. |
| 2018/0296743 A1 | 10/2018 | Siegenthaler |
| 2018/0303991 A1 | 10/2018 | Nusser et al. |
| 2018/0311421 A1 | 11/2018 | Tuseth et al. |
| 2019/0001034 A1 | 1/2019 | Taskin et al. |
| 2019/0125948 A1 | 5/2019 | Stanfield et al. |
| 2019/0143018 A1 | 5/2019 | Salahieh et al. |
| 2019/0275224 A1 | 9/2019 | Hanson et al. |
| 2019/0298902 A1 | 10/2019 | Siess et al. |
| 2019/0328948 A1 | 10/2019 | Salahieh et al. |
| 2019/0358382 A1 | 11/2019 | Delgado, III |
| 2020/0076271 A1 | 3/2020 | Sconzert et al. |
| 2020/0121835 A1 | 4/2020 | Farago et al. |
| 2020/0306434 A1 | 10/2020 | VanCamp et al. |
| 2020/0316277 A1 | 10/2020 | Delgado, III |
| 2021/0008264 A1 | 1/2021 | Radman |
| 2021/0046231 A1 | 2/2021 | Weber et al. |
| 2021/0052793 A1 | 2/2021 | Struthers et al. |
| 2021/0060223 A1 | 3/2021 | Weber et al. |
| 2021/0060224 A1 | 3/2021 | Kronstedt et al. |
| 2021/0069393 A1 | 3/2021 | Schauer et al. |
| 2021/0069397 A1 | 3/2021 | Chouinard et al. |
| 2021/0100940 A1 | 4/2021 | Breidall et al. |
| 2021/0162196 A1 | 6/2021 | Georges et al. |
| 2021/0220634 A1 | 7/2021 | Cook |
| 2021/0220636 A1 | 7/2021 | Schauer et al. |
| 2021/0220637 A1 | 7/2021 | Edwards et al. |
| 2021/0260360 A1 | 8/2021 | Georges et al. |
| 2021/0275796 A1 | 9/2021 | Struthers et al. |
| 2021/0316277 A1 | 10/2021 | Im et al. |
| 2021/0316278 A1 | 10/2021 | Kim et al. |
| 2021/0346680 A1 | 11/2021 | Vogt et al. |
| 2022/0080179 A1 | 3/2022 | Earles et al. |
| 2022/0080182 A1 | 3/2022 | Earles et al. |
| 2022/0080183 A1 | 3/2022 | Earles et al. |
| 2022/0080184 A1 | 3/2022 | Clifton et al. |
| 2022/0080185 A1* | 3/2022 | Clifton ............... A61M 60/237 |
| 2022/0080186 A1 | 3/2022 | Clifton et al. |
| 2022/0226634 A1 | 7/2022 | Gross-Hardt et al. |
| 2022/0257920 A1 | 8/2022 | Earles et al. |

FOREIGN PATENT DOCUMENTS

| | | |
|---|---|---|
| WO | WO 98/00185 A1 | 1/1988 |
| WO | WO 00/33446 | 6/2000 |
| WO | WO 01/10342 A1 | 2/2001 |
| WO | WO 02/070039 A2 | 9/2002 |
| WO | WO 03/103745 A2 | 12/2003 |
| WO | WO 2005/016416 A1 | 2/2005 |
| WO | WO 2005/020848 A2 | 3/2005 |
| WO | WO 2009/046779 A1 | 4/2009 |
| WO | WO 2009/091968 A1 | 7/2009 |
| WO | WO 2017/165372 A1 | 9/2017 |
| WO | WO 2019/094963 A1 | 5/2019 |
| WO | WO 2019/173596 | 9/2019 |
| WO | WO 2021/062565 | 4/2021 |
| WO | WO 2021/062566 | 4/2021 |
| WO | WO 2021/113389 | 6/2021 |
| WO | WO 2021/117021 | 6/2021 |
| WO | WO 2021/119413 | 6/2021 |
| WO | WO 2021/138673 | 7/2021 |

OTHER PUBLICATIONS

European Search Report, EP09175307.9, dated Dec. 18, 2009.

Herzum, M. et al., Managing a complication after direct stenting; removal of a maldeployed stent with rotational artherectomy, Heart Jrnl 2005: 91: e46, URL: http://www.heartjnl.com/cgi/content/full/91/6/e46).

Written Opinion of the International Searching Authority, PCT/US2005/028875, dated Dec. 15, 2005.

International Search report of PCT/US2005/028875, dated Dec. 16, 2005.

International Search Report and Written Opinion for PCT/US2013/033894, dated Jun. 17, 2013.

International Search Report and Written Opinion for PCT/US2020/062928, dated Apr. 9, 2021, 26 pages.

International Search Report and Written Opinion for PCT/US2020/064489, dated Apr. 8, 2021, 25 pages.

Notice of Allowance dated Oct. 1, 2021, in U.S. Appl. No. 15/276,590, 14 pages.

Greenberg, B. et al., Rationale, Design and Methods for a Pivotal Randomized Clinical Trial of Continuous Aortic Flow Augmentation in Patients with Exacerbation of Heart Failure: The Momentum Trial, Journal of Cardiac Failure, 2007, vol. 13, No. 9, pp. 715-721.

Siess, T. et al., "From a lab type to a product: A retrospective view on Impella's assist technology," Artificial Organs, Jan. 15, 2002, vol. 25, Issue 5, pp. 414-421.

Triantafyllou, K.D. et al., Coronary endarterectomy and stent removal with of-pump coronary artery bypass surgery, Heart Journal, Images in Cardiology, dai: 10.1136/hrt.2005.076687, p. 885.

(56) References Cited

OTHER PUBLICATIONS

Vazquez, R. et al., Plasma protein denaturation with graded heat exposure, Perfusion, 2013, vol. 28, No. 6, pp. 557-559.

* cited by examiner

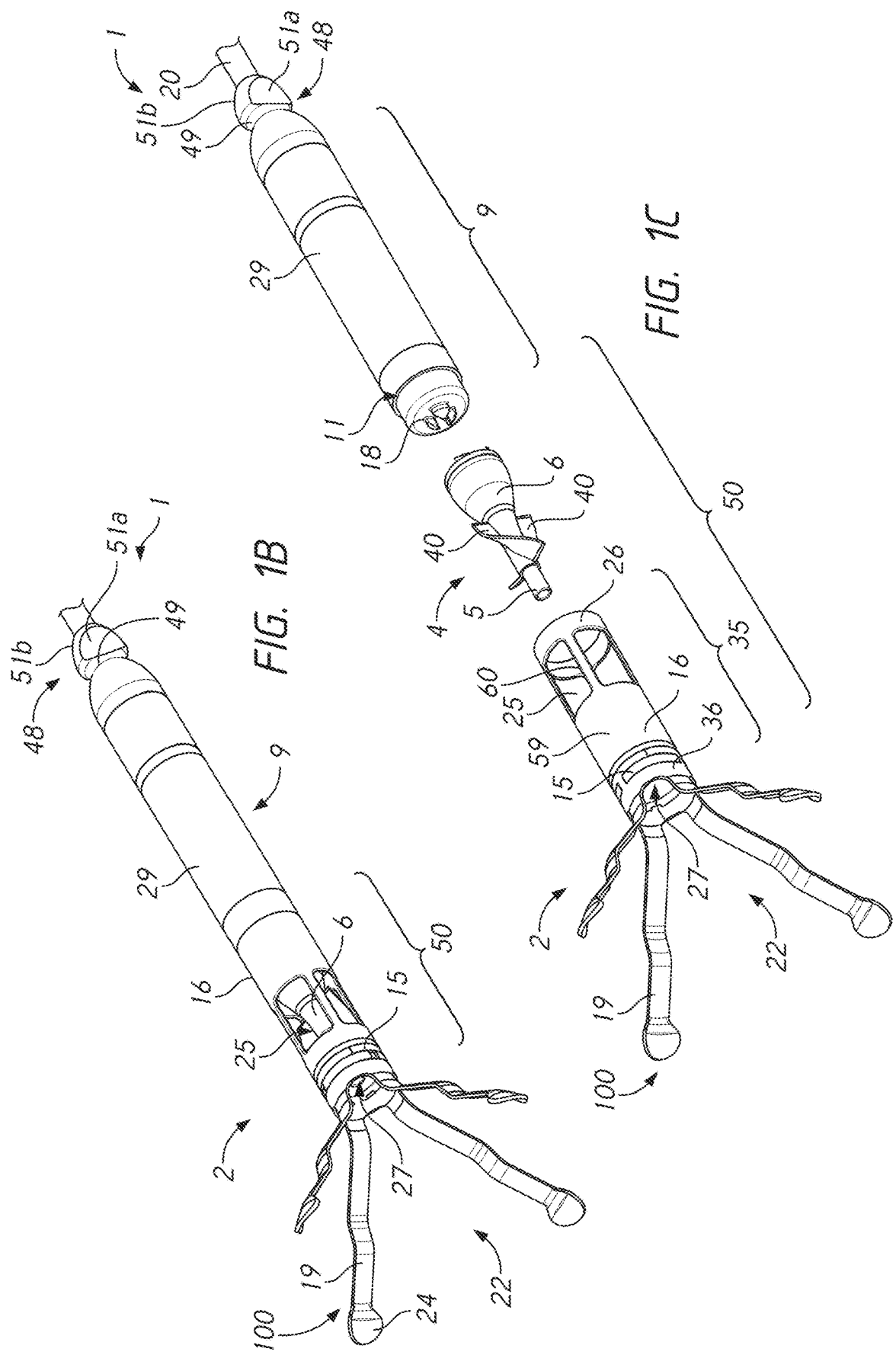

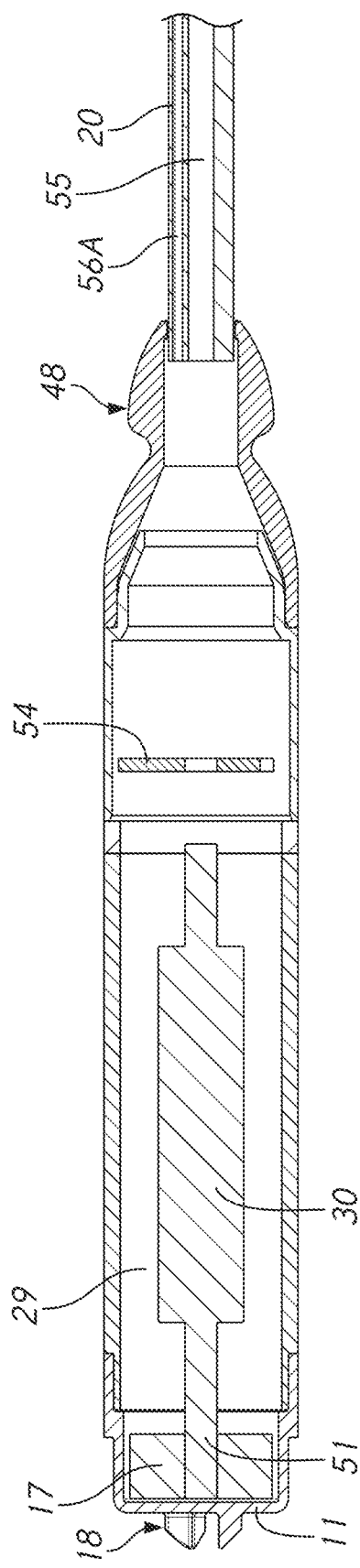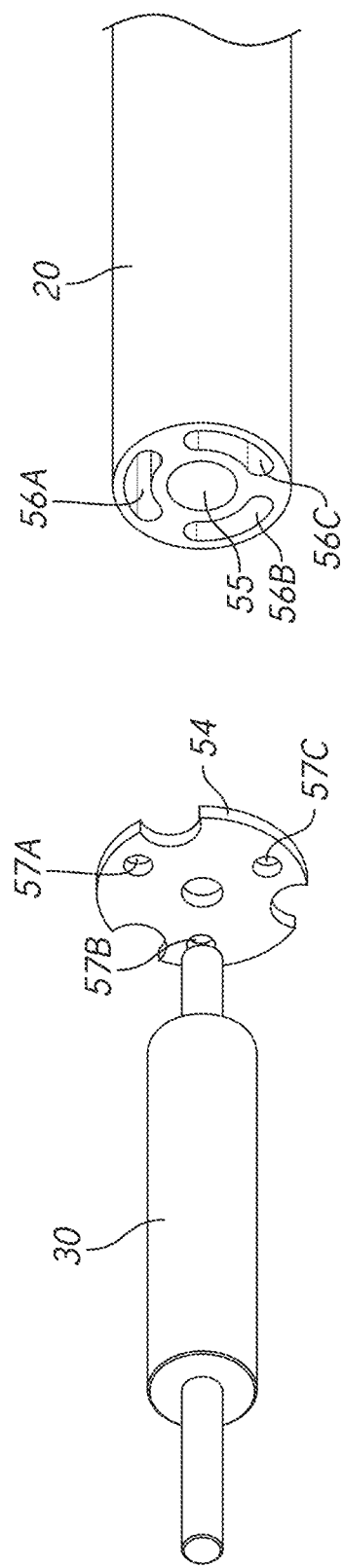

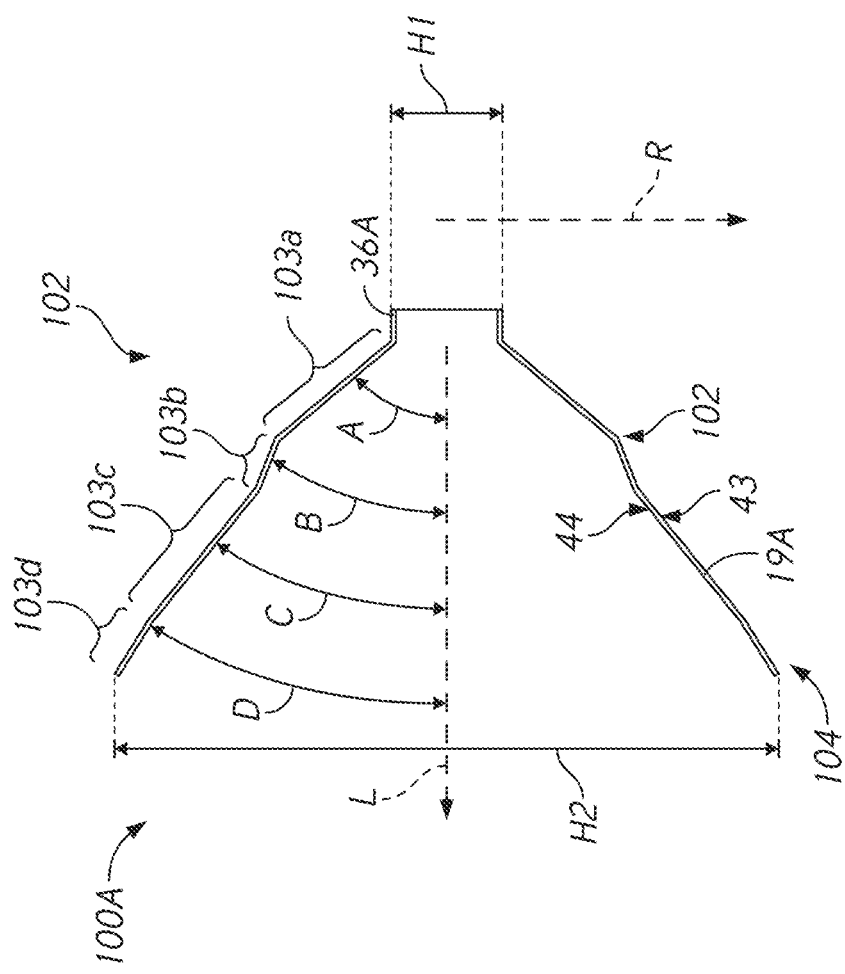
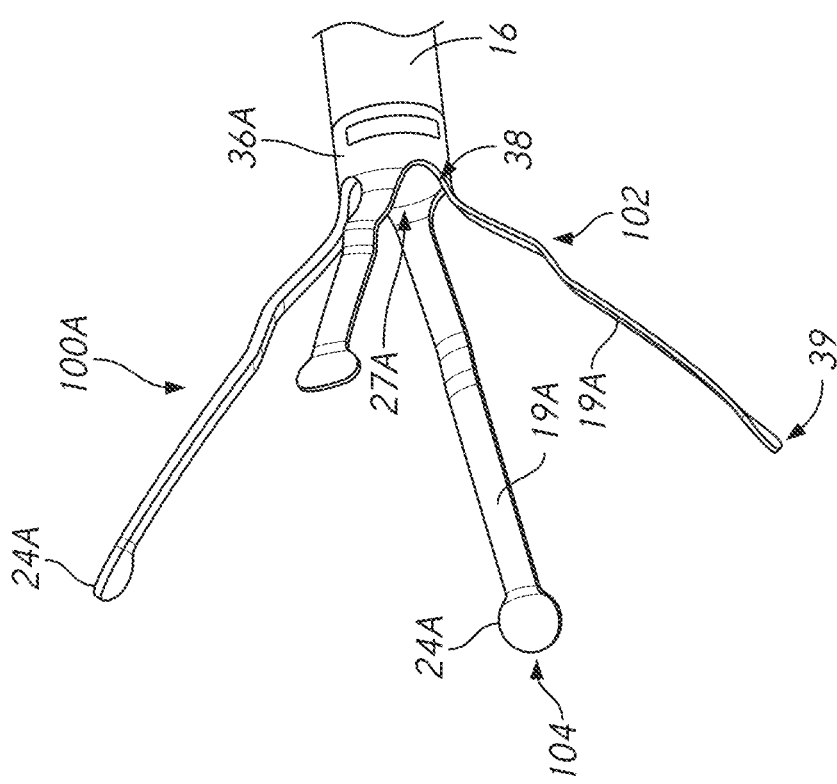
FIG. 2B
FIG. 2A

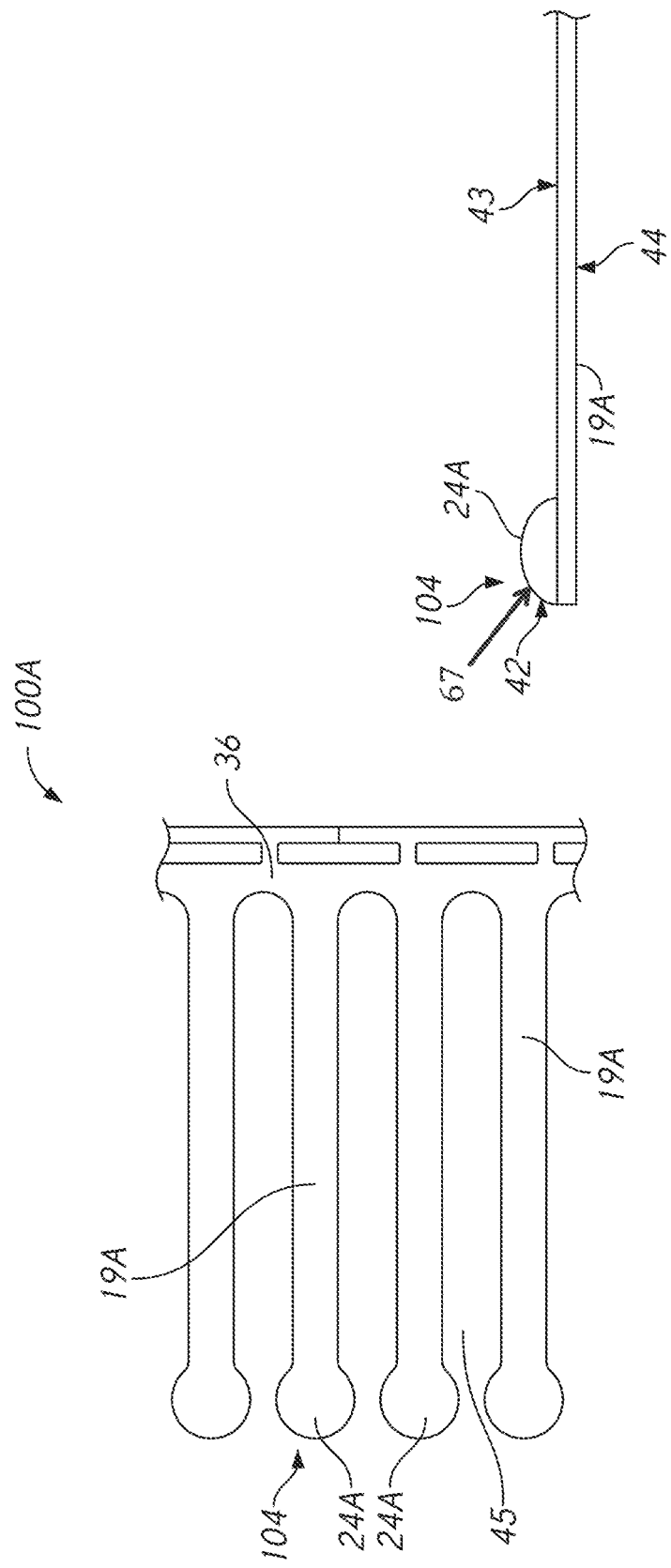

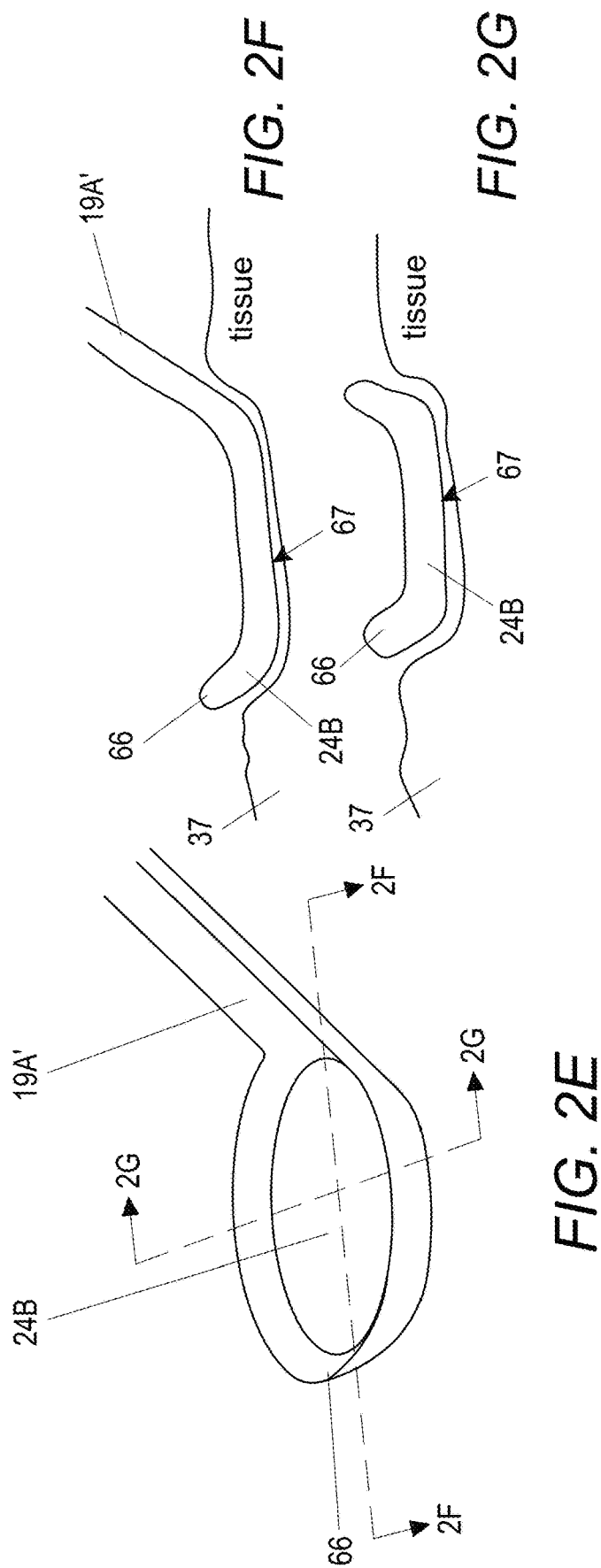

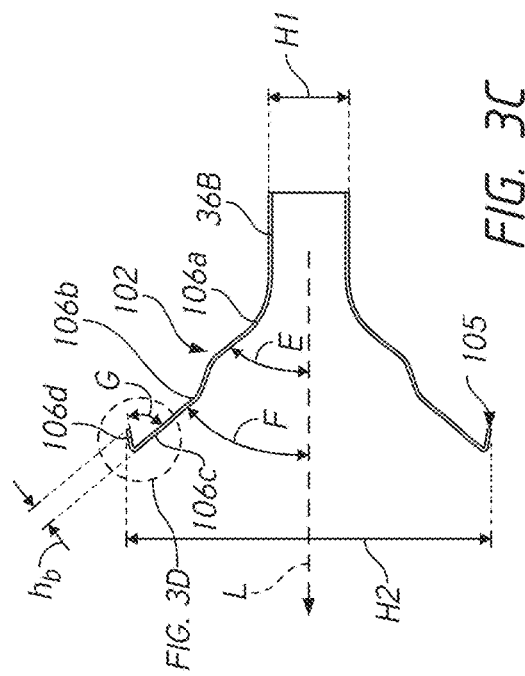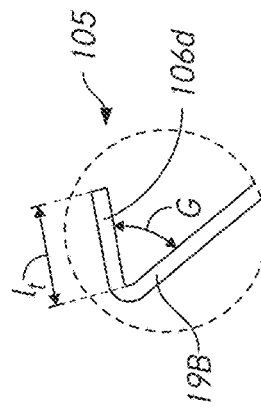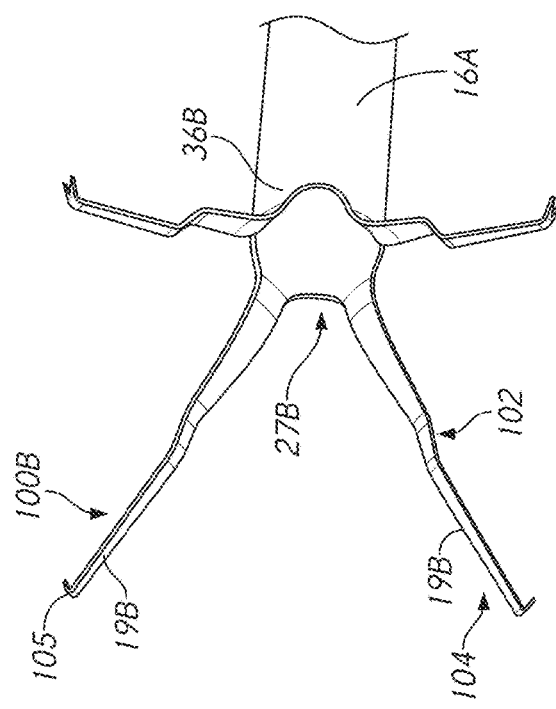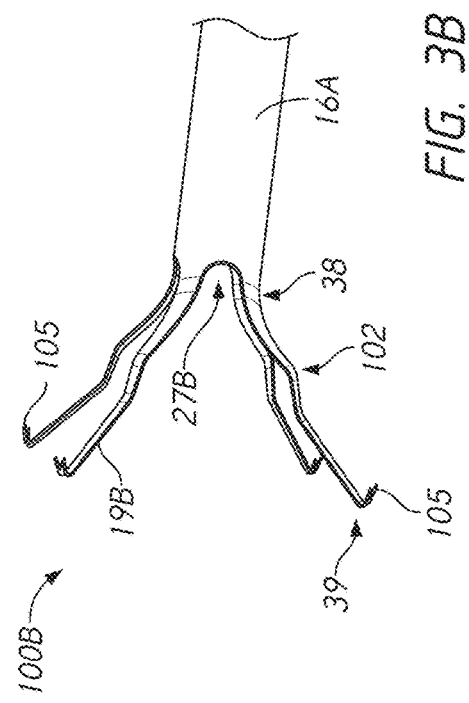

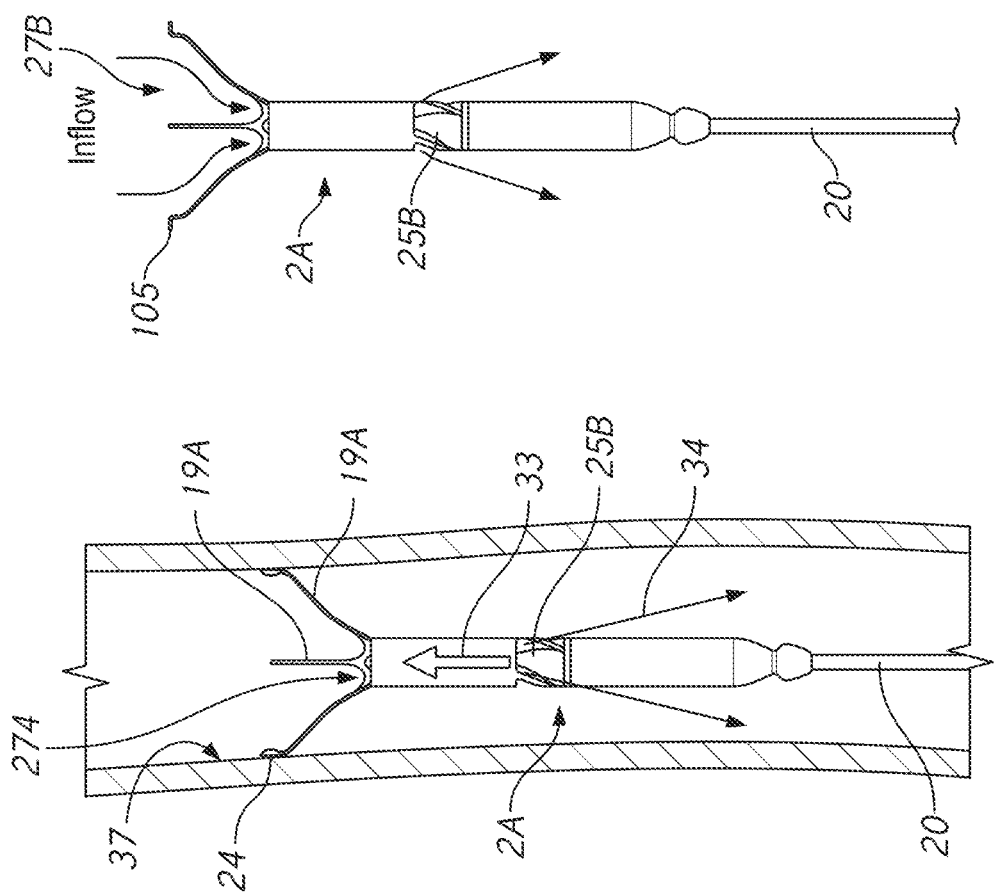
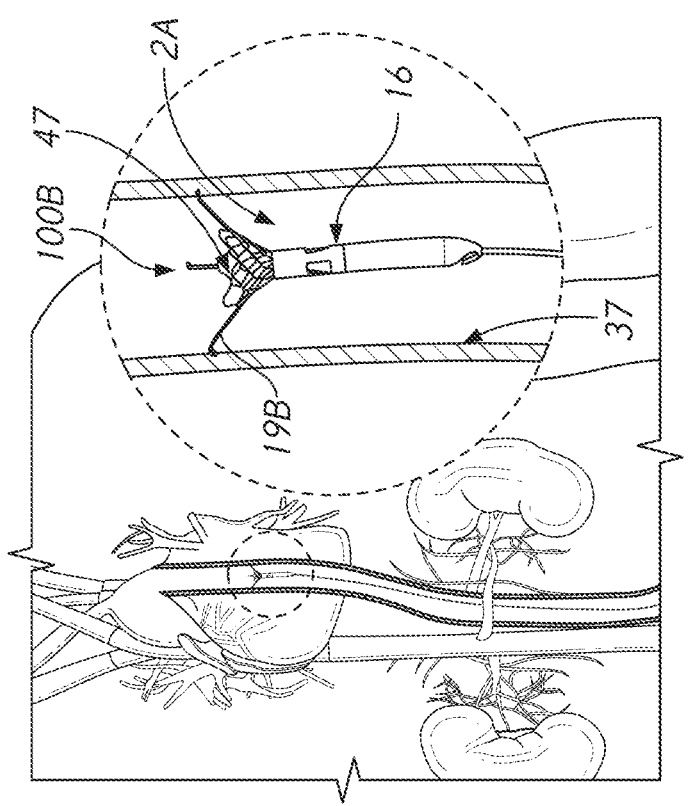
FIG. 4E
FIG. 4D
FIG. 4C

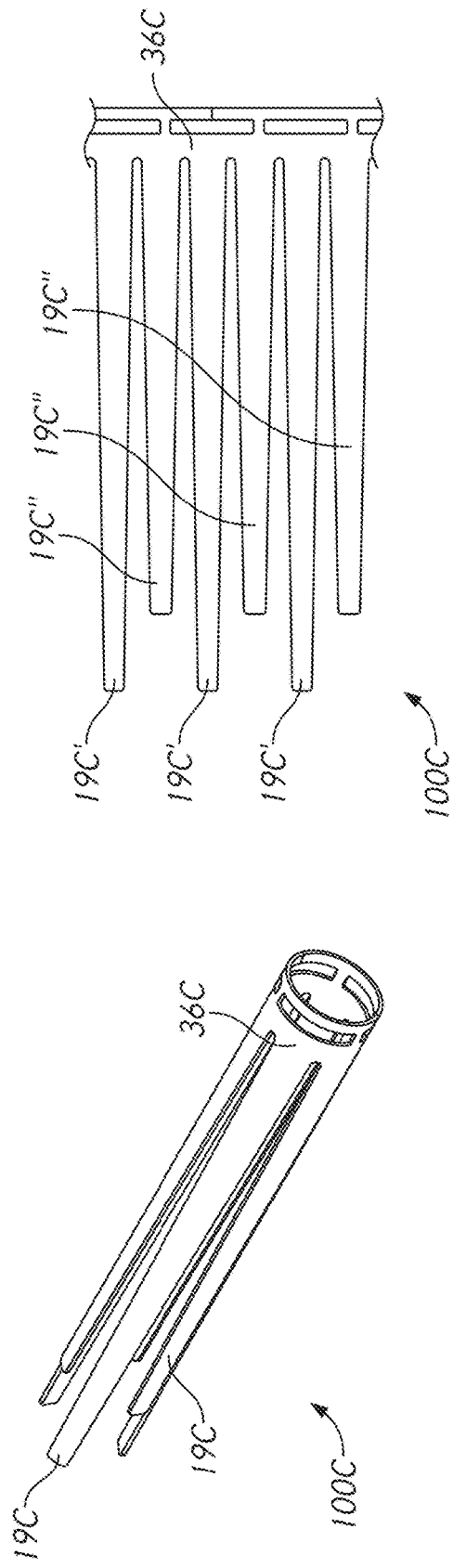
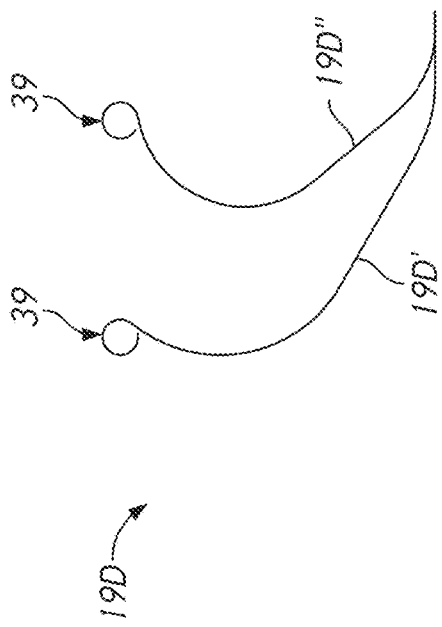

SUPPORT STRUCTURES FOR INTRAVASCULAR BLOOD PUMPS

INCORPORATION BY REFERENCE TO ANY PRIORITY APPLICATIONS

This application is a continuation of U.S. application Ser. No. 17/535,330, filed Nov. 24, 2021, which claims priority to International Application No. PCT/US2020/064489, filed Dec. 11, 2020, which claims priority to U.S. Provisional Patent Application No. 62/947,940, filed Dec. 13, 2019, the entire contents of which are hereby incorporated by reference herein in their entirety and for all purposes. This application also claims priority to International Application No. PCT/US2020/062928, filed Dec. 2, 2020, which claims priority to U.S. Provisional Patent Application No. 62/943,062, filed Dec. 3, 2019, the entire contents of each of which are hereby incorporated by reference herein in their entirety and for all purposes. Any and all applications for which a foreign or domestic priority claim is identified in the Application Data Sheet as filed with the present application are hereby incorporated by reference under 37 CFR 1.57.

BACKGROUND

Field

The field relates to localization and positioning structures and methods for intravascular blood pumps.

Description of the Related Art

In the field of cardiac assist devices and mechanical circulatory support, blood pumps are used to support the heart in circulating blood through the body. Some of these blood pumps are intravascular blood pumps and are designed or adapted for use within blood vessels.

Some intravascular blood pumps have been described as including hooks to fix the intravascular pump to the inner wall of the vessel. Hooks prevent translation of the device along the axis of the vessel and rotation of the device about the axis of the vessel through direct local contact.

SUMMARY OF THE INVENTION

A support or localization structure for a pump that may limit or prevent translation, limit or prevent rotation, aid in maintaining the position of some part of the pump relative to some anatomical structure, or any combination of these is needed. The localization structure may be designed for acute, semi-acute, semi-chronic, or chronic use.

Blood is a harsh environment for devices and any thrombus, foreign material, or pathogen in a blood vessel could have dire consequences. Novel localization structures that are biocompatible, non-thrombogenic, and non-hemolytic for well in excess of the expected duration of use are needed. Additionally, the function and removal of novel means of localization should preferentially be consistent with any endothelialization that may occur during the expected duration of use.

Novel localization structures for intravascular devices preferably provide biocompatibility of materials and surfaces, design for hemodynamic compatibility (reduced or minimal flow mediated thrombogenicity and hemolysis and disruption to natural flow), reduced or minimal trauma to the inside of the vessel or other anatomical structures, sufficient localization and freedom of motion, and removability when the therapy that the localized device provides is complete.

Localization and positioning systems and methods for medical devices, such as intravascular blood pumps or other intravascular devices are disclosed herein. The various embodiments comprise one or more of the following elements: struts extending from the device to be localized, said struts providing constant or intermittent contact with the vessel wall; a tether (e.g., a power lead) to limit translation and aid in positioning; and propulsion to maintain localization.

In some embodiments, the localization and positioning system may be part of or include a support structure that comprises struts that are projections that extend distally and radially outward from the device to contact the blood vessel walls or other anatomical features. Various illustrated embodiments show the struts extending distal the pump housing and impeller. However it should be appreciated that, alternatively, any of the struts may instead extend proximal the pump head (e.g., proximal the motor housing). In such embodiments, one or more of the struts can extend proximally from the drive unit or shroud. In yet other embodiments, one or more, e.g., a first plurality of struts can extend distal the pump housing and impeller, and one or more, e.g., a second plurality of struts can extend proximal the pump head (e.g., proximal the motor housing). The struts may be shaped, formed, and processed so that for a given outward radial force in the expanded configuration, the radial force in the collapsed configuration and/or the force to move from the expanded to collapsed configuration is reduced (e.g., minimized).

Struts may consist of or otherwise be formed from a biocompatible metal, shape memory alloy, or alloy, like nitinol, and may be designed to have a particular shape and/or geometry. Through constant or intermittent contact with the inner wall of the blood vessel or some other anatomical feature, struts can provide localization or positioning or both. A device to be positioned may have multiple sets of struts and these may project from the device at one or more angles or at any angle. In some embodiments, the struts may have features like hooks. In other embodiments, the struts may have pads to interface with the surface of the blood vessel wall. For use with intravascular devices, struts may have a collapsed configuration for fitting within a sheath and an expanded configuration to provide localization and/or positioning. In some embodiments the struts may have knees (or kinks or bends) to prevent hooks or other features from contacting the inner wall of a sheath in a collapsed configuration. The struts may be shaped, formed, and processed so that for a given outward radial force in the expanded configuration, the radial force in the collapsed configuration and/or the force required to move from the expanded to collapsed configuration is reduced or minimized.

In some embodiments, the localization, stabilization, and positioning system (or support structure) may comprise one or more tethers that connect the device to be localized and/or positioned to one or more anchor or contact points. Tethers may be flexible and may preferentially limit translation or rotation in one direction. In some embodiments, the tethers may have an additional function. As one nonlimiting example, a tether may also comprise a power lead that transmits electrical power to the device to be localized or positioned.

In some embodiments, the localization, stabilization, and positioning system may comprise a means of propulsion (e.g., a pump in various embodiments). In cases where the device to be localized and/or positioned is an intravascular blood pump, the pumping of blood is a key function of the device in some embodiments. The propulsive or reactive force generated by blood pumping may be used as part of the localization and positioning system.

In some embodiments, the localization and/or positioning system may comprise combinations of the above elements that together provide unique benefits or advantages.

The discussion herein has outlined rather broadly various features of the present disclosure in order that the detailed description that follows may be better understood. Additional features and advantages of the disclosure will be described hereinafter.

In one embodiment, a blood flow assist system is disclosed. The blood flow assist system can include or consist essentially of an impeller disposed in a pump housing of a pump, the pump comprising a longitudinal axis, the impeller generating a thrust force when operating in a blood vessel to pump blood; and a tether extending away from the pump housing, the tether configured to oppose loads applied in opposite directions at opposite ends thereof. In some embodiments, a longitudinal component of the thrust force generated by the impeller directed along the longitudinal axis of the pump is opposed by the tether, the tether configured to maintain a position of the pump within the blood vessel without requiring contact between the pump and a blood vessel wall of the blood vessel.

In some embodiments, the system includes a support structure coupled to or formed with the pump housing, the support structure configured to at least intermittently contact the blood vessel wall to maintain spacing of the pump housing from the blood vessel wall in which the pump housing is disposed. In some embodiments, the support structure comprises a plurality of elongate struts having a first end coupled with the pump housing and a second end opposite the first end, each elongate strut of the plurality of struts having a slender body and extending between the first end and the second end. In some embodiments, the system includes convex contact pads disposed at respective distal portions of the plurality of struts, the convex contact pads configured to at least intermittently contact the blood vessel wall to maintain spacing of the pump housing from a blood vessel wall in which the pump housing is disposed. In some embodiments, the plurality of struts includes a first plurality of struts and a second plurality of struts, wherein, when the plurality of struts are in an expanded configuration, first contact pads of the first plurality of struts are configured to engage with the blood vessel wall at a first longitudinal position and second contact pads of the second plurality of struts are configured to engage with the blood vessel wall at a second longitudinal position that is spaced from the first longitudinal position. In some embodiments, the contact pads are configured to be disposed distal and radially outward of the pump housing and to be reversibly deflectable to hold the pump housing within the blood vessel to hold the pump housing away from the blood vessel wall. In some embodiments, the contact pads comprise a convex periphery surrounding a convex blood vessel engagement surface. In some embodiments, the contact pads comprise a convex profile in a cross-sectional plane disposed transverse to a longitudinal axis of the pump. In some embodiments, the tether comprises a conductor configured to convey current to a motor operatively coupled to the impeller from a source connectable to a proximal end of the tether. In some embodiments, the system includes the pump further comprises a motor housing coupled to a proximal portion of the pump housing, the motor disposed in the motor housing. In some embodiments, the tether comprises a rotatable drive shaft connected to a motor to be disposed outside a body of the patient. In some embodiments, a kit comprises the blood flow assist system and a sheath sized and shaped to receive the pump housing, the tether, and the support structure.

In another embodiment, a blood flow assist system is disclosed. The blood flow assist system can include or consist essentially of an impeller disposed in a pump housing of a pump, the pump comprising a longitudinal axis, the impeller generating a thrust force when operating in a blood vessel to pump blood; a tether extending away from the pump housing, the tether configured to oppose loads applied in opposite directions at opposite ends thereof; and a support structure.

In some embodiments, the support structure comprises convex contact pads configured to at least intermittently contact a blood vessel wall to maintain spacing of the pump housing from a blood vessel wall in which the pump housing is disposed. In some embodiments, the system can include a motor operatively coupled with the impeller. In some embodiments, the tether comprises a hollow, elongate member enclosing a conductor disposed therein, the conductor configured to convey current to and from the motor from a source connectable to a proximal end of the tether, the tether configured to oppose loads applied in opposite directions at opposites ends thereof. In some embodiments, the system includes a plurality of elongate struts having a first end coupled with a second end of the pump and a second end opposite the first end, each elongate strut of the plurality of elongate struts comprising a slender body extending between the first end and the second end, each strut of the plurality of elongate struts being configured to store strain energy when a transverse load is applied. In some embodiments, the blood flow assist system includes a contact pad disposed at the second end of each of the elongate struts of the plurality of elongate struts, each contact pad having an enlarged width compared to a width of the immediately adjacent expanse of the corresponding elongate strut of the plurality of elongate struts. In some embodiments, in use, a longitudinal component of the thrust force generated by the impeller directed along the longitudinal axis of the pump is opposed by the tension member of the tether.

In some embodiments, the contact pad comprises a generally circular pad having a diameter greater than the width of the immediately adjacent expanse of the corresponding elongate struts. In some embodiments, the elongate struts comprise at least one inflection along the slender body thereof to facilitate folding of the struts into a lumen of a sheath. In some embodiments, each of the contact pads comprises a smooth surface free of sharp edges or hooks. In some embodiments, each of the contact pads comprises a convex cross-sectional profile on a blood vessel facing side thereof. In some embodiments, each of the contact pads comprises a spherical portion. In some embodiments, the elongate struts are configured to apply a load to an aortic wall when deployed to locally radially expand vessel wall tissue against which the contact pad is apposed. In some embodiments, the contact pad comprises a hole configured to allow blood vessel wall tissue to be received therein. In some embodiments, each of the contact pads comprises one or more scalloped edges to allow blood vessel wall tissue to be received therein. In some embodiments, each of the contact pads comprises a domed portion. In some embodiments, the hollow, elongate member is configured to receive a stiffening member to facilitate introduction of the pump housing. In some embodiments, the pump further comprises a motor housing coupled to a proximal portion of the pump housing, the motor disposed in the motor housing. In some embodiments, a transverse component of the thrust force directed transverse to the longitudinal axis of the pump is opposed by strain energy stored in at least one of the elongate struts of the plurality of elongate struts upon deflection of one or more of the elongate struts of the plurality of struts. In some embodiments, a kit comprises the blood flow assist system and a sheath sized and shaped to receive the pump housing, the motor, the tether, and the plurality of elongate struts.

In some embodiments, the support structure comprises a plurality of elongate struts having a first end coupled with a second end of the pump and a second end opposite the first end, each elongate strut of the plurality of struts having a slender body and extending between the first end and the second end, the convex contact pads disposed at respective distal portions of the plurality of struts. In some embodiments, the plurality of struts includes a first plurality of struts and a second plurality of struts, wherein, when the plurality of struts are in an expanded configuration, first contact pads of the first plurality of struts are configured to engage with the blood vessel wall at a first longitudinal position and second contact pads of the second plurality of struts are configured to engage with the blood vessel wall at a second longitudinal position that is spaced from the first longitudinal position. In some embodiments, in a collapsed configuration of the struts, at least a portion of the struts has a major lateral dimension that is no more than a major lateral dimension of the pump housing. In some embodiments, the contact pads are configured to be disposed distal and radially outward of the pump housing and to be reversibly deflectable to hold the pump housing within the blood vessel to hold the pump housing away from the blood vessel wall. In some embodiments, the contact pads comprise a convex periphery surrounding a convex blood vessel engagement surface. In some embodiments, the contact pads comprise a convex profile in a cross-sectional plane disposed transverse to a longitudinal axis of the pump. In some embodiments, the tether comprises a conductor configured to convey current to a motor operatively coupled to the impeller from a source connectable to a proximal end of the tether. In some embodiments, the pump further comprises a motor housing coupled to a proximal portion of the pump housing, the motor disposed in the motor housing. In some embodiments, the tether comprises a rotatable drive shaft connected to a motor to be disposed outside a body of the patient.

In another embodiment, a blood flow assist system is disclosed. The blood flow assist system can include or consist essentially of an impeller disposed in a pump housing of a pump; and a support structure comprising a plurality of struts coupled to or formed with the pump housing, the support structure having an expanded configuration in which the plurality of struts extend outwardly relative to the pump housing and a collapsed configuration in which the pump is disposed in a sheath, wherein, in the collapsed configuration, at least a portion of the struts has a major lateral dimension that is no more than a major lateral dimension of the pump housing. In some embodiments, the major lateral dimension of the at least the portion of the struts is less than the major lateral dimension of the pump housing. In some embodiments, the blood flow assist system includes a motor housing and a motor disposed in the motor housing, wherein the major lateral dimension of the at least the portion of the struts is less than a major lateral dimension of the motor housing. In some embodiments, the blood flow assist system includes convex contact pads at a distal portion of the struts, the convex contact pads configured to contact a blood vessel wall to maintain spacing of the pump housing from a blood vessel wall in which the pump housing is disposed.

In another embodiment, a blood flow assist system is disclosed. The blood flow assist system can include or consist essentially of an impeller disposed in a pump housing of a pump; and a support structure comprising a plurality of struts coupled to or formed with the pump housing, the support structure having an expanded configuration in which the plurality of struts extend outwardly relative to the pump housing and a collapsed configuration in which the pump is disposed in a sheath, wherein the plurality of struts includes a first plurality of struts and a second plurality of struts, wherein, when the plurality of struts are in an expanded configuration, first contact pads of the first plurality of struts are configured to engage with the blood vessel wall at a first longitudinal position and second contact pads of the second plurality of struts are configured to engage with the blood vessel wall at a second longitudinal position that is spaced from the first longitudinal position. In some embodiments, the blood flow assist system includes convex contact pads at a distal portion of the plurality of struts, the convex contact pads configured to at least intermittently contact a blood vessel wall to maintain spacing of the pump housing from a blood vessel wall in which the pump housing is disposed. In some embodiments, a major lateral dimension of the at least a portion of the struts is less than a major lateral dimension of the pump housing. In some embodiments, the blood flow assist system includes a tether extending away from the pump housing, the tether configured to oppose loads applied in opposite directions at opposite ends thereof.

In another embodiment, a blood flow assist system is disclosed. The blood flow assist system can include or consist essentially of an impeller disposed in a pump housing of a pump, the pump comprising a longitudinal axis, the impeller generating a thrust force when operating in a blood vessel to pump blood; a tether coupled with a first end of the pump; and a support structure comprising a contact pad resiliently deflectable toward and away from a longitudinal axis of the pump, a free state of the contact pad being spaced away from the longitudinal axis of the pump by a distance greater than a half-width of a blood vessel into which the pump housing is to be deployed, the contact pad applying sufficient force to a wall of the blood vessel to depress a portion of the contact pad into the wall such that a surrounding portion of the vessel wall is radially inward from a contact surface of the contact pad. In some embodiments, the contact pad is configured to engage without hooking the wall of the blood vessel when applied. In some embodiments, the contact pad comprises an elongate member and an enlarged blood vessel wall contact surface disposed at the end of the elongate member. In some embodiments, the tether comprises a conductor configured to convey current from a source connectable to a proximal end of the tether to a motor operatively coupled with the impeller.

In another embodiment, a blood flow assist system is disclosed. The blood flow assist system can include or consist essentially of a pump comprising: an impeller disposed in a pump housing; and a strut comprising a first end disposed at or coupled with the pump housing, a second end opposite the first end, and an inflection zone disposed between the first end and the second end, the second end elastically deflectable toward and away from a longitudinal axis of the pump, a free state of the strut spacing the second end thereof away from the longitudinal axis of the pump, the second end of the strut configured to engage a wall of the blood vessel. The system can include or consist essentially of a sheath comprising an inner wall configured to be disposed over the pump and to deflect the strut between the first and the second end thereof; wherein the inflection zone is configured such that when the strut is deflected by the inner wall of the sheath, the second end of the strut is spaced away from the inner wall of the sheath. In some embodiments, the second end of the strut comprises a hook. In some embodiments, the inflection zone comprises an S-connection between a first span of the strut and a second span of the strut, the first span and the second span being disposed along parallel trajectories. In some embodiments, the blood flow assist system includes a tether coupled with a first end of the pump, the tether comprising an electrical conveyance comprising a conductor configured to convey current to and from a source connectable to a proximal end of the electrical conveyance.

In another embodiment, a method of operating a blood flow assist system. The method can include or consist essentially of providing a pump at a treatment location within a blood vessel of a patient, the pump including a pump housing disposed in a sheath, an impeller disposed in the pump housing, and a plurality of elongate struts extending from the pump housing in a collapsed configuration, each elongate strut of the plurality of struts including a convex contact pad at a distal end thereof; providing relative motion between the sheath and the pump to remove the pump from the sheath, the plurality of elongate struts radially self-expanding to an expanded configuration in which at least one convex contact pad at least intermittently makes contact with a vessel wall of the blood vessel to maintain spacing of the pump from the vessel wall; and rotating the impeller to pump blood. In some embodiments, the method includes conveying electrical current to a motor by way of a tether comprising a conductor, the motor operatively coupled with the impeller and the tether coupled to the pump, wherein rotating the impeller generates a thrust force, the tether opposing the thrush force. In some embodiments, the method includes percutaneously delivering the sheath to the treatment location, and, subsequently, delivering the pump to the treatment location. In some embodiments, the method includes causing a portion of the contact pad to depress into the vessel wall. In some embodiments, the method includes removing the pump from the patient.

In another embodiment, a method of operating a blood flow assist system is disclosed. The method can include or consist essentially of providing a pump at a treatment location within a blood vessel of a patient, the pump including a pump housing disposed in a sheath, an impeller disposed in the pump housing, and a plurality of elongate struts extending distally from the pump housing in a collapsed configuration; providing relative motion between the sheath and the pump to remove the pump from the sheath, the plurality of elongate struts radially self-expanding to an expanded configuration in which at least one contact pad at an end of at least one strut of the plurality of elongate struts at least intermittently makes contact with a vessel wall of the blood vessel to maintain spacing of the pump from the vessel wall, the at least one contact pad applying sufficient force to the vessel wall of the blood vessel to depress a portion of the contact pad into the vessel wall such that a surrounding portion of the vessel wall is radially inward from the contact pad; and rotating the impeller to pump blood. In some embodiments, the method includes percutaneously delivering the sheath to the treatment location, and, subsequently, delivering the pump to the treatment location. In some embodiments, the method includes removing the pump from the patient. In some embodiments, the method includes conveying electrical current to a motor by way of a tether comprising a conductor, the motor operatively coupled with the impeller and the tether coupled to the pump.

In another embodiment, a method of manufacturing a blood flow assist system is disclosed. The method can include or consist essentially of providing an impeller in a pump housing of a pump, the pump disposed along a longitudinal axis, the impeller generating a thrust force when operating in a blood vessel to pump blood; coupling a tether with a first end of the pump; and coupling a support structure to a second end of the pump, the support structure comprising convex contact pads configured to at least intermittently contact a blood vessel wall to maintain spacing of the pump housing from a blood vessel wall in which the pump housing is disposed. In some embodiments, the method includes providing the motor in a motor housing of the pump, the motor housing disposed distal the pump housing. In some embodiments, the support structure comprises a plurality of elongate struts having a first end coupled with the second end of the pump and a second end opposite the first end, each elongate strut of the plurality of struts having a slender body and extending between the first end and the second end, each strut of the plurality of elongate struts being configured to store strain energy when a transverse load is applied to the second ends of the struts of the plurality of elongate struts. In some embodiments, the method includes patterning the plurality of elongate struts. In some embodiments, patterning comprises laser cutting the plurality of elongate struts from a sheet of material.

In another embodiment, a method of operating a blood flow assist system is disclosed. The method can include or consist essentially of providing a pump at a treatment location within a blood vessel of a patient, the pump including a pump housing disposed in a sheath, an impeller disposed in the pump housing, and a tether extending proximally from the pump housing to outside the patient, the tether configured to oppose loads applied in opposite directions at opposite ends thereof; providing relative motion between the sheath and the pump to remove the pump from the sheath; rotating the impeller to pump blood and to generate a thrust force, wherein a longitudinal component of the thrust force generated by the impeller directed along a longitudinal axis of the pump is opposed by the tether, the tether configured to maintain a position of the pump within the blood vessel without requiring contact between the pump and a blood vessel wall of the blood vessel. In some embodiments, the pump includes a plurality of elongate struts extending distally from the pump housing in a collapsed configuration, each elongate strut of the plurality of struts including a convex contact pad at a distal end thereof, wherein providing relative motion comprises causing the plurality of elongate struts to radially self-expand to an expanded configuration in which at least one convex contact pad makes at least intermittent contact with a vessel wall of the blood vessel to maintain spacing of the pump from the vessel wall.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 1B is a schematic perspective view of a pump at a distal portion of the blood flow assist system of FIG. 1A.

FIG. 1C is a schematic perspective, partially-exploded view of the pump of FIG. 1B.

FIG. 1D is a schematic side sectional view of a motor housing according to various embodiments.

FIG. 1E is a schematic perspective view of a motor and a motor mount support.

FIG. 1F is a schematic perspective view of a distal end of a power lead having lumens shaped to received conductors that are configured to supply power to the motor.

FIG. 2A is an image showing a front perspective view of a localization system, according to one embodiment.

FIG. 2B is a schematic side view of the localization system of FIG. 2A.

FIG. 2C is a schematic plan view of a laser cut pattern for the localization system of FIG. 2B.

FIG. 2D is a schematic side plan view of a strut having a dome- or spherical-shaped contact pad.

FIG. 2E is a schematic perspective view of a contact pad that pillows into a blood vessel wall, according to some embodiments.

FIG. 2F is a schematic front sectional view of the contact pad shown in FIG. 2E.

FIG. 2G is a schematic side sectional view of the contact pad shown in FIG. 2E.

FIG. 3A is an image of a front perspective of a localization system according to another embodiment.

FIG. 3B is an image of a side view of the localization system of FIG. 3A.

FIG. 3C is a schematic side view of the localization system of FIGS. 3A-3B.

FIG. 3D is a schematic enlarged view of the second end of the strut of FIGS. 3A-3C.

FIG. 3G illustrates a plan view of a distal end of the strut of FIG. 3D.

FIGS. 4A-4E show a method of delivering and deploying a localization and positioning system that incorporates struts with contact pads, a tether, and propulsive force.

FIG. 5A is a schematic perspective view of a localization system in a collapsed configuration, according to another embodiment.

FIG. 5B is a schematic plan view of a laser cut design for the system of FIG. 5A.

FIG. 6 is a schematic side view of a plurality of struts according to various embodiments.

DETAILED DESCRIPTION

Figure 1A:
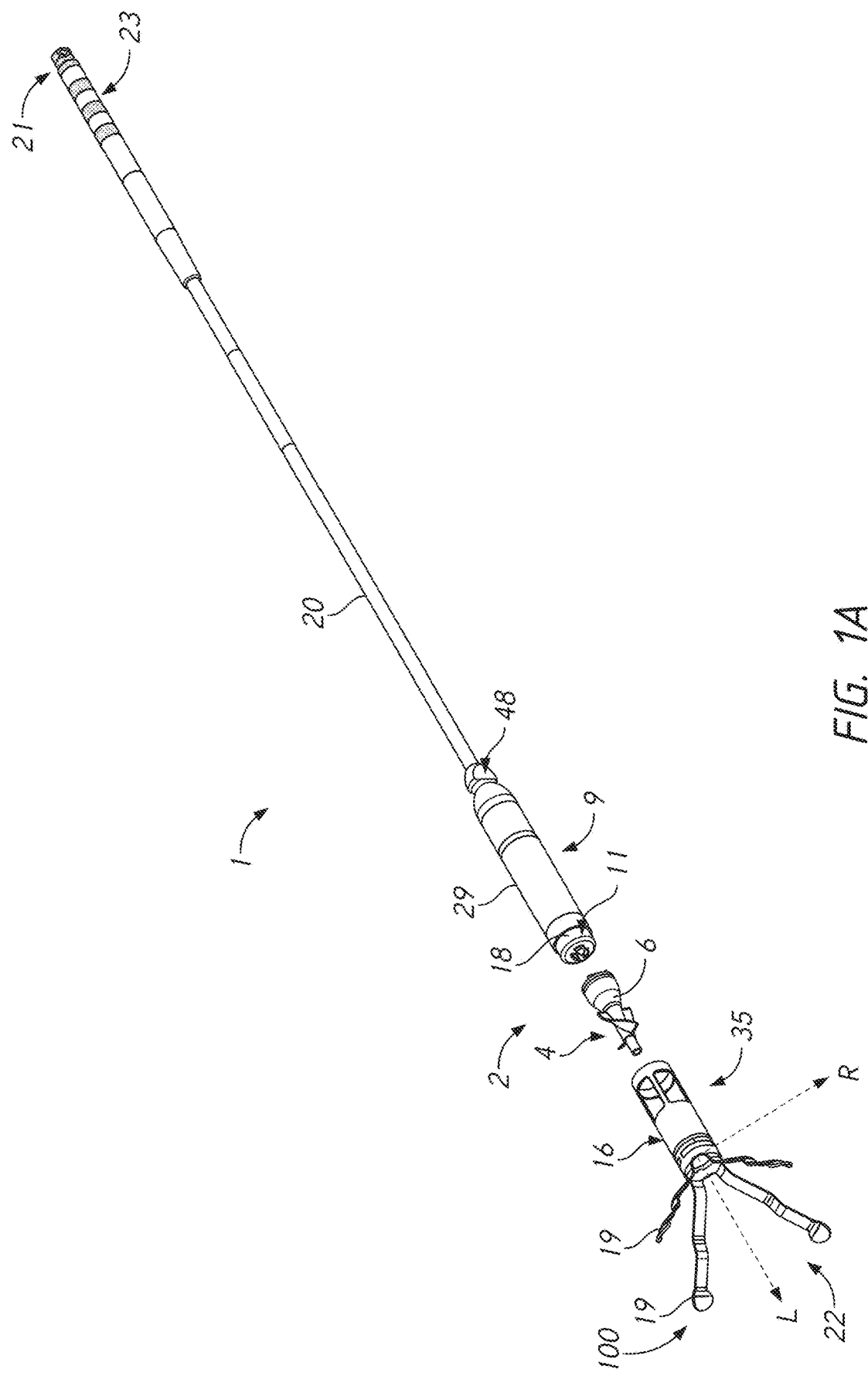
FIG. 1A is a schematic perspective, partially-exploded view of a blood flow assist system, according to various embodiments.

Refer now to the drawings wherein depicted elements are not necessarily shown to scale and wherein like or similar elements are designated by the same reference numeral through the several views.

Referring to the drawings in general, it will be understood that the illustrations are for the purpose of describing particular implementations of the disclosure and are not intended to be limiting thereto. While most of the terms used herein will be recognizable to those of ordinary skill in the art, it should be understood that when not explicitly defined, terms should be interpreted as adopting a meaning presently accepted by those of ordinary skill in the art.

I. Overview of Blood Flow Assist Systems

Various embodiments disclosed herein relate to a blood flow assist system 1 configured to provide circulatory support to a patient, as illustrated in FIGS. 1A-1I. The system 1 can be sized for intravascular delivery to a treatment location within the circulatory system of the patient, e.g., to a location within the descending aorta of the patient. As shown in FIG. 1A, the system 1 can have a proximal end 21 with a connector 23 configured to connect to an external control system, e.g., a console (not shown). The connector 23 can provide electrical communication between the control system and a power lead 20 extending distally along a longitudinal axis L from the connector 23 and the proximal end 21. The power lead 20 can comprise an elongate body that electrically and mechanically connects to a pump 2 at or near a distal end 22 of the blood flow assist system 1, with the distal end 22 spaced apart from the proximal end 21 along the longitudinal axis L. As explained herein, the power lead 20 can also serve as a flexible tether configured to oppose loads applied in opposite directions at opposite ends of the power lead 20.

Figure 1G:
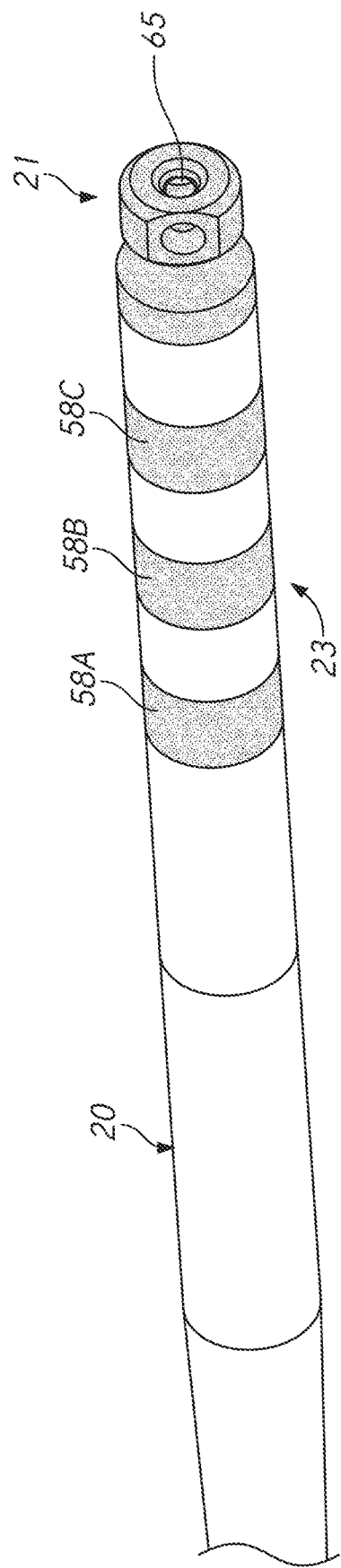
FIG. 1G is a schematic perspective view of a proximal end portion of the power lead.
Figure 1H:
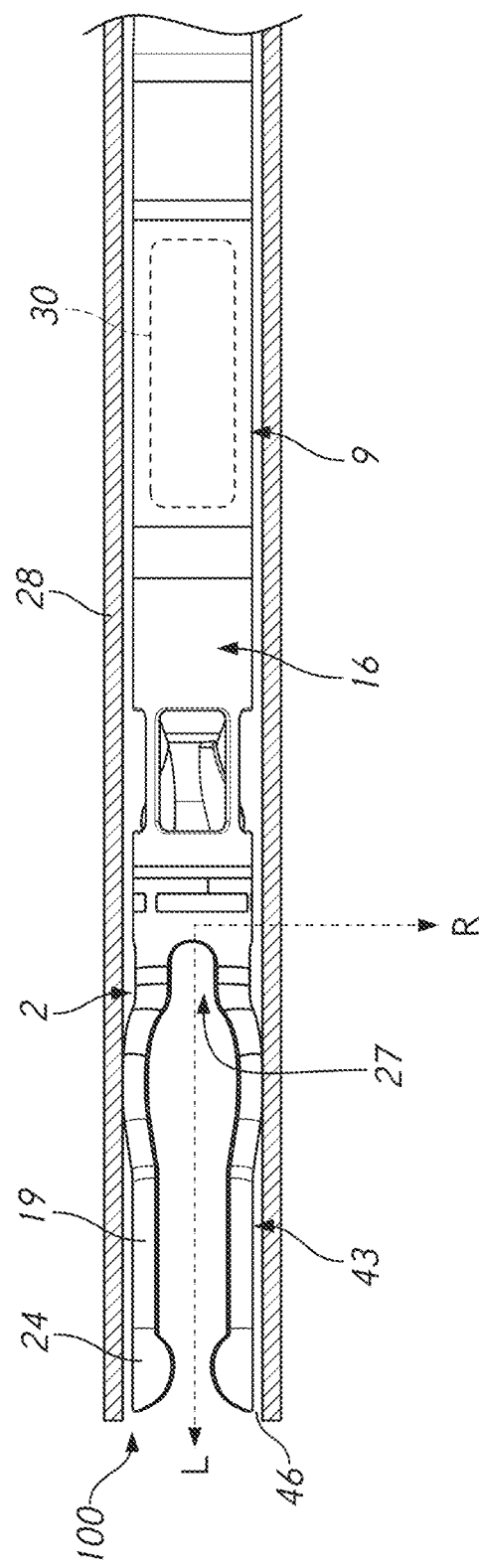
FIG. 1H is a schematic side view of the pump disposed in a collapsed configuration in a delivery sheath.
Figure 1I:
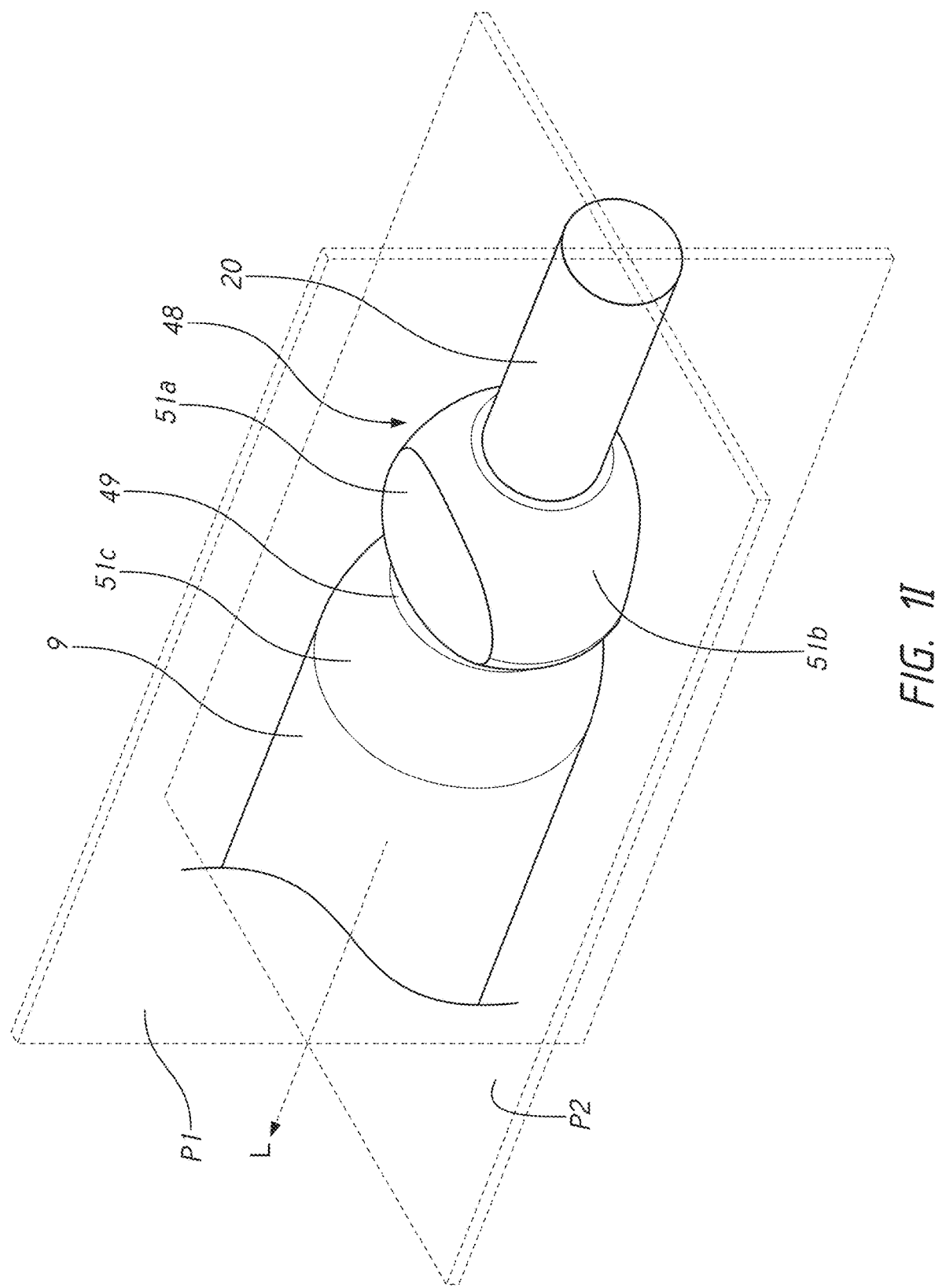
FIG. 1I is a schematic perspective view of a retrieval feature used to remove the pump, according to some embodiments.

The pump 2 can comprise a pump head 50 including a pump housing 35 connected to a drive unit 9 that includes a motor housing 29. A retrieval feature 48 can be provided at a proximal end portion of the pump 2. In some embodiments, the retrieval feature can be coupled with the distal end of the power lead 20 between the power lead 20 and the motor housing 29. After a procedure, the clinician can remove the pump 2 from the patient by engaging a tool (e.g., a snare, a clamp, hook, etc.) with the retrieval feature 48 to pull the pump 2 from the patient. For example, the retrieval feature 48 can comprise a neck 49 (e.g., a reduced diameter section) at a proximal curved portion 51*c* of the motor housing 29 and an enlarged diameter section disposed proximal the neck 49. The enlarged diameter section can comprise a first curved portion 51*a* and a second curved portion 51*b*, as shown in FIGS. 1B, 1C, and 1I. The first and second curved portions 51*a*, 51*b* can comprise convex surfaces, e.g., convex ball portions. The first and second curved portions 51*a*, 51*b* can have different radii of curvature. For example, as shown in FIG. 1I, the first curved portion 51*a* can have a larger radius of curvature than the second curved portion 51*b*. The first curved portion 51*a* can be disposed on opposing sides of the retrieval feature 48 in some embodiments. The second curved portion 51*b* can be disposed around the first curved portion 51*a* and can have a radially-outward facing surface and a proximally-facing convex surface coupled to the distal end of the power lead 20. The neck 49 can have a first depth at a first circumferential position of the retrieval feature 48 and a second depth less than the first depth at a second circumferential position of the retrieval feature 48 spaced apart from the first circumferential position.

Beneficially, as shown in FIG. 1I, one or more first planes P1 extending parallel to the longitudinal axis L and intersecting the first curved portion 51*a* can have a first angle or taper between the proximal curved portion 51*c* of the motor housing 29 and the first curved portion 51a. One or more second planes P2 extending parallel to the longitudinal axis L and intersecting the second curved portion 51b can have a second angle or taper (which is different from the first angle or taper) between the proximal curved portion 51c of the motor housing 29 and the second curved portion 51b. The first angle or taper can provide a gradual, continuous (generally monotonically decreasing) geometric transition between the proximal curved portion 51c of the motor housing 29 and the power lead 20, which can provide for smooth blood flow and reduce the risk of thrombosis. The second curved portion 51b can serve as a lobe that extends radially outward, e.g., radially farther out than the first curved portion 51a. The second curved portion 51b can be used to engage with a retrieval device or snare to remove the pump 2 from the anatomy. Some cross sections through the longitudinal axis of the retrieval feature 48 can contain a substantial neck (e.g., a local minimum in the radius of curvature measured along its central axis) while other cross sections through the longitudinal axis of the retrieval feature 48 can contain an insubstantial local minimum or no local minimum. In the illustrated embodiment, there are two first curved portions 51a that can serve as a dual lobe retrieval feature. In other embodiments, more or fewer lobes can be provided to enable pump retrieval while ensuring smooth flow transitions between the motor housing 29 and power lead 20.

As shown in FIGS. 1B-1C, 1E, and 1I, the neck 49 can be disposed between the curved portions 51a, 51b and a proximally-facing convex surface 51c of the motor housing 29. In the illustrated embodiment, the retrieval feature 48 can be coupled to or integrally formed with the motor housing 29. In other arrangements, the retrieval feature 48 can be disposed at other locations of the pump 2. As shown, the retrieval feature 48 can be symmetrical and continuously disposed about the longitudinal axis L. In other arrangements, the retrieval feature 48 can comprise a plurality of discrete surfaces spaced apart circumferentially and/or longitudinally. In the illustrated embodiments, the motor housing 29 (and motor) can be part of the pump 2 and disposed inside the vasculature of the patient in use. In other embodiments, however, the motor housing 29 (and motor) can be disposed outside the patient and a drive cable can connect to the impeller 6.

As shown in FIGS. 1A-1C, the drive unit 9 can be configured to impart rotation to an impeller assembly 4 disposed in the pump housing 35 of the pump head 50. As explained herein, the drive unit 9 can include a drive magnet 17 (see FIG. 1D) and a motor 30 (see FIGS. 1D-1E) disposed in the motor housing 29 capped by a distal drive unit cover 11. The motor 30 is shown schematically in FIG. 1D. The drive unit cover 11 can be formed with or coupled to a drive bearing 18. The drive magnet 17 can magnetically couple with a corresponding driven or rotor magnet (not shown) of the impeller assembly 4 that is disposed proximal the impeller 6 within the shroud 16. The power lead 20 can extend from the treatment location to outside the body of the patient, and can provide electrical power (e.g., electrical current) and/or control to the motor 30. Accordingly, no spinning drive shaft extends outside the body of the patient in some embodiments. As explained herein, the power lead 20 can energize the motor 30, which can cause the drive magnet 17 to rotate about the longitudinal axis L, which can serve as or be aligned with or correspond to an axis of rotation. Rotation of the drive magnet 17 can impart rotation of the rotor magnet and a primary or first impeller 6 of the impeller assembly 4 about the longitudinal axis L. For example, as explained herein, the rotor magnet (which can be mechanically secure to an impeller shaft 5) can cause the impeller shaft 5 (which can serve as a flow tube) and the first impeller 6 to rotate to pump blood. In other embodiments, the drive unit 9 can comprise a stator or other stationary magnetic device. The stator or other magnetic device can be energized, e.g., with alternating current, to impart rotation to the rotor magnet. In the illustrated embodiments, the impeller 6 can have one or a plurality of blades 40 extending radially outward along a radial axis R that is radially transverse to the longitudinal axis L. For example, the first impeller 6 can have a plurality of (e.g., two) longitudinally-aligned blades 40 that extend radially outwardly from a common hub and that have a common length along the longitudinal axis L. The curvature and/or overall profile can be selected so as to improve flow rate and reduce shear stresses. Skilled artisans would appreciate that other designs for the first impeller 5 may be suitable.

As shown in FIGS. 1A-1C, the impeller assembly 4 can be disposed in a shroud 16. The impeller shaft 5 can be supported at a distal end by a sleeve bearing 15 connected to a distal portion of the shroud 16. A support structure such as a localization system 100 (discussed further below) can comprise a base portion 36 coupled with the sleeve bearing 15 and/or the shroud 16. In some embodiments, the base portion 36, the sleeve bearing 15, and/or the shroud 16 can be welded together. In other embodiments, the sleeve bearing 15 and/or the shroud 16 can be formed as one part. The base portion 36 of the support structure or localization system 100 (which can be part of or serve as a support structure), the sleeve bearing 15, and the shroud 16 can cooperate to at least partially define the pump housing 35, as shown in FIGS. 1A and 1C. The localization system 100 can comprise a plurality of self-expanding struts 19 having convex contact pads 24 configured to contact a blood vessel wall to maintain spacing of the pump housing 35 from the wall of the blood vessel in which the pump housing 35 is disposed. In FIGS. 1A-1C, the struts 19 of the localization system 100 are illustrated in an expanded, deployed configuration, in which the contact pads 24 extend radially outward to a position in which the contact pads 24 would contact a wall of a blood vessel within which the pump 2 is disposed to at least partially control position and/or orientation of the pump head 50 relative to the blood vessel wall, e.g., to anchor, the pump 2 during operation of the system 1.

A first fluid port 27 can be provided distal the impeller assembly 4 at a distal end of the pump housing 35. The shroud 16 can comprise a proximal ring 26 coupled with the motor housing 29 and a plurality of second fluid ports 25 formed in a proximal portion of the shroud 16 adjacent (e.g., immediately distal) the proximal ring 26. As shown in FIG. 1C, the second fluid ports 25 can comprise openings formed between axially-extending members 60 (also referred to as pillars) that extend along the longitudinal axis L (which may also serve as a longitudinal axis of the pump head 2 and/or pump housing 35) between the proximal ring 26 and a cylindrical section 59 of the shroud 16. In some embodiments, the axially-extending members 60 can be shaped or otherwise be configured to serve as vanes that can shape or direct the flow of blood through the second fluid ports 25. For example, in various embodiments, the axially-extending members 60 can be angled, tapered, or curved (e.g., in a helical pattern) to match the profile of the impeller blades 40 and/or to accelerate blood flow through the pump 2. In other embodiments, the axially-extending members 60 may not be angled to match the blades 40. In some embodiments, the first fluid port 27 can comprise an inlet port into which blood flows. In such embodiments, the impeller assembly 4 can draw blood into the first fluid port 27 and can expel the blood out of the pump 2 through the second fluid ports 25, which can serve as outlet ports. In other embodiments, however, the direction of blood flow may be reversed, in which case the second fluid ports 25 may serve as fluid inlets and the first fluid port 27 may serve as a fluid outlet.

As shown in FIGS. 1A-1D, the system 1 comprises the drive unit 9 with the motor 30 that can be sealed in the motor housing 29. The drive magnet 17 can be rotatable by the motor 30 by way of a motor shaft 51. The motor 30 can electrically connect to the power lead 20. The power lead 20 can serve as a flexible tether that comprises an elongate tension member configured to oppose loads applied in opposite directs at opposite ends of the power lead 20. In one embodiment the power lead 20 is hollow, as discussed further below. As shown in FIGS. 1D and 1F, the power lead 20 can comprise an insulating body having a central lumen 55 and a plurality of (e.g., three) outer lumens 56A-56C extending along a length of the power lead 20. One or more electrical conductors can be disposed in the hollow elongate power lead 20 and can be configured to convey current to the motor 30 from a source, such as the external control system. For example, in some embodiments, the outer lumens 56A-56C can be sized and shaped to receive corresponding electrodes or electrical wires (not shown) to provide electrical power to the motor 30. For example, the lumens 56A-56C can receive, wires configured to supply ground and drive voltage to corresponding windings on the motor. The electrodes can extend through corresponding openings 57A-57C of a motor mounting support 54 configured to support the motor 30. The central lumen 55 can be sized and shaped to receive an elongate stiffening member or guidewire (not shown). The stiffening member or guidewire can be inserted through an opening 65 at the proximal end 21 (see FIG. 1G) into the central lumen 55 during delivery to help guide the pump 2 to the treatment location or maintain the pump 2 in a given location. The stiffening member or guidewire can be easily inserted and removed when finished. As shown in FIG. 1G, the connector 23 near the proximal end 21 of the system 1 can have electrical contacts 58A-58C electrically connected to the wires or conductors in the corresponding outer lumens 56A-56C. The contacts 58A-58C can comprise rings spaced apart by an insulating material and can be configured to electrically connect to corresponding electrical components in the control system or console (not shown).

Beneficially, the blood flow assist system 1 can be delivered percutaneously to a treatment location in the patient. FIG. 1H shows the pump 2 disposed within an elongate sheath 28. As shown, the struts 19 are held in a collapsed configuration by the inner wall of the sheath 28. As discussed further below, the struts 19 can be configured to collapse in a controlled manner, e.g., with at least a portion deflected away from inner wall of the sheath 28 when disposed in the sheath. As shown, the struts 19 can comprise knees 102, which can serve to space distal ends of the struts 19 (e.g., at or near the contact pads 24 or hooks) from the inner wall of the sheath 28, such that there is a space 46 between the contact pads 24 or hooks and the inner wall of the sheath 28 in the collapsed configuration within the sheath 28.

The knees 102 can be of the same configuration for each of the struts 19 in one embodiment. In such an embodiment, the struts 19 may all collapse or fold in the same manner within the sheath 28. In another embodiment the knee 102 of one or more struts 19 can be differentiated from the knee 102 of one or more other struts 19 such that the struts are collapsed or folded in different manners. As explained herein, in various embodiments, the struts can be longitudinally-aligned or longitudinally-offset or staggered. For example, a pair of opposing struts 19 (e.g., disposed radially opposite one another) can have knees 102 that cause the opposing strut of the pair to collapse prior to the collapsing of other struts 19 of the pump 2. In one example, the pump 2 has four struts 19. Two opposing struts 19 are configured to bend at the knees 102 prior to the bending of the knees of the other struts 19. As such, the two opposing struts 19 can be collapsed to a position between the other two struts to provide a compact arrangement. The knees 102 can be configured such that some struts undergo a greater degree of bending or collapsing. Thus the space 46 between the contact pads 26 and the inner wall of the sheath 28 can be two to six (and in some cases three to four) times greater for one or more, e.g., a pair of, struts than for one or more, e.g., another pair of struts 19, which can be provided to avoid tangling of the struts. Accordingly, in various embodiments, some struts may be structured to collapse first when engaged with the sheath 28, and the remaining struts can collapse as the sheath 28 induces the collapsing of the initial struts.

In some embodiments, one or more struts comprises knees 102 that can control the order of collapsing of the struts. For example one or more struts can have a knee 102 positioned more proximally compared to the position of the knees 102 of one or more other struts. In one example, two opposing struts 19 can have knees 102 disposed more proximally than are the knees 102 of another strut 19. In one example, a first set of opposing struts 19 have knees 102 disposed more proximally than a second set of struts 19 disposed approximately 90 degrees offset from the first set of struts 19. This can allow the first set of struts to be more completely folded by distal advancement of the sheath 28 before a more complete folding of the second set of struts 19. In a further variation, knees 102 can be longitudinally spaced apart on adjacent struts 19 so that adjacent struts fold at different times or rates. The illustrated embodiments includes the knees 102, but in other embodiments, no knees may be provided. For example, the struts 19 can be retracted at different rates by hinges and/or by modifying material thickness or properties in or along the length of one or more struts 19 to control the timing or rate of folding upon advancing the sheath 28. A living hinge structure can be formed along the length of one or more struts 19 to control timing, rate, and/or sequence of retraction of the struts 19. In one example, an area of reduced thickness transverse to the length of a strut 19 causes the strut to fold or bend when a sheath is advanced across the reduced thickness area. By offsetting the longitudinal position of reduced thickness areas in the struts 19, the sequence of retraction can be controlled.

In the collapsed configuration, the struts 19 can be compressed to a diameter or major lateral dimension at one or more locations that is approximately the same as (or slightly smaller than) the diameter of the shroud 16. Thus, as shown in the collapsed configuration of FIG. 1H, at least a portion of the struts 19 are compressed to a diameter or major lateral dimension that is smaller than the major lateral dimension or diameter of the pump housing 35, shroud 16 and/or the drive unit 9. In some embodiments, at least a portion of the struts has a major lateral dimension that is no more than a major lateral dimension of the pump housing 35. In some embodiments, at least a portion of the struts has a major lateral dimension that is less than a major lateral dimension of the pump housing 35 and/or the motor housing 29. The patient can be prepared for the procedure in a catheterization lab in a standard fashion, and the femoral artery can be accessed percutaneously or by a surgical approach. The sheath 28 (or a dilator structure within the sheath 28) can be passed over a guidewire and placed into the treatment location, for example, in the descending aorta. After the sheath 28 is placed (and the dilator removed), the pump 2 can be advanced into the sheath 28, with the pump 2 disposed in the mid-thoracic aorta, approximately 4 cm below the takeoff of the left subclavian artery. In other embodiments, the pump 2 and sheath 28 can be advanced together to the treatment location. Positioning the pump 2 at this location can beneficially enable sufficient cardiac support as well as increased perfusion of other organs such as the kidneys. Once at the treatment location, relative motion can be provided between the sheath 28 and the pump 2 (e.g., the sheath 28 can be retracted relative to the pump 2, or the pump 2 can be advanced out of the sheath 28). The struts 19 of the localization system can self-expand radially outwardly along the radial axis R due to stored strain energy into the deployed and expanded configuration shown in FIGS. 1A-1C. In some embodiments, such as those in which the vasculature is accessed by the femoral artery, the struts 19 can extend distally, e.g., distally beyond a distal end of the shroud 16 and/or the impeller 6. In other embodiments, as explained herein, the pump 2 can be delivered percutaneously through a subclavian artery. In such embodiments, the struts 19 may extend proximally, e.g., proximal the pump housing 35 and/or the motor housing 29. In still other embodiments, multiple pluralities of struts may extend proximally and distally relative to the pump 2. The convex contact pads 24 can engage the blood vessel wall to stabilize (e.g., assist in anchoring) the pump 2 in the patient's vascular system. Once at the treatment location, the clinician can engage the control system to activate the motor 30 to rotate the impeller assembly 4 to pump blood.

Thus, in some embodiments, the pump 2 can be inserted into the femoral artery and advanced to the desired treatment location in the descending aorta. In such arrangements, the pump 2 can be positioned such that the distal end 22 is upstream of the impeller 6, e.g., such that the distally-located first fluid port 27 is upstream of the second fluid port(s) 25. In embodiments that access the treatment location surgically or percutaneously via the femoral artery, for example, the first fluid port 27 can serve as the inlet to the pump 2, and the second ports 25 can serve as the outlet(s) of the pump 2. The struts 19 can extend distally beyond a distal end of the pump housing 35. In other embodiments, however, the pump 2 can be inserted percutaneously through the left subclavian artery and advanced to the desired treatment location in the descending aorta. In such arrangements, the pump 2 can be positioned such that the distal end 22 of the system 1 is downstream of the impeller 6, e.g., such that the distally-located first fluid port 27 is downstream of the second fluid port(s) 25. In embodiments that access the treatment location through the left subclavian artery, the second fluid port(s) 25 can serve as the inlet(s) to the pump 2, and the first port 27 can serve as the outlet of the pump 2.

When the treatment procedure is complete, the pump 2 can be removed from the patient. For example, in some embodiments, the pump can be withdrawn proximally (and/or the sheath 28 can be advanced distally) such that a distal edge of the sheath 28 engages with a radially-outer facing surface 43 of the struts 19. In some embodiments, the distal edge of the sheath 28 can engage with the knees 102 of the struts (see, e.g., FIGS. 2A-3C). The distal edge of the sheath 28 can impart radially-inward forces to the radially-outer facing surface 43 (e.g., at approximately the location of the knees 102) to cause the struts 19 to collapse and be drawn inside the sheath 28. Relative motion opposite to that used for deploying the pump 2 can be provided between the sheath 28 and the pump 2 (e.g., between the sheath 28 and the impeller assembly 4 and pump housing 35) to collapse the struts 19 into the sheath 28 in the collapsed configuration. In some embodiments, the pump 2 can be withdrawn from the sheath 28 with the sheath 28 in the patient's body, and the sheath 28 can be subsequently used for another procedure or removed. In other embodiments, the sheath 28 and the pump 2 can be removed together from the patient's body.

Figure 1J:
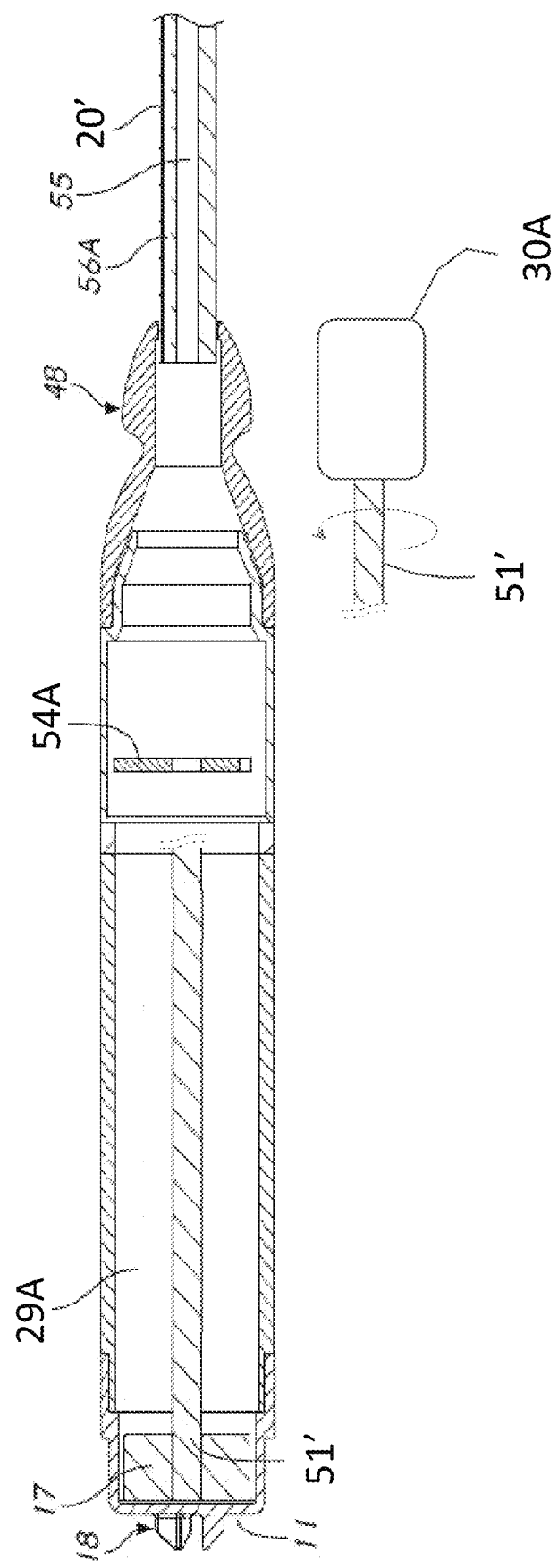
FIG. 1J is a cross-sectional view of an alternative embodiment in which a drive shaft is coupled to a motor configured to be disposed outside the patient when the pump is in use.

The foregoing description includes embodiments in which a proximal end of a drive shaft 51 is located in the drive unit 9. The proximal end of the drive shaft 51 and the motor 30 are disposed within the body in use. FIG. 1J shows another embodiment in which a motor 30A is disposed outside the body in use. An elongate, flexible shaft 51' is coupled at a distal end with the drive magnet 17. The shaft 51' extends through an elongate body 20' and is or can be coupled at a proximal end thereof with a motor 30A. The motor 30A can be larger than the motor 30 since it need not be disposed within the profile of the sheath 28. The elongate body 20' may have one or more lumens. The shaft 51' may extend through the central lumen 55. One or more outer lumens 56a may be provided to flow a fluid into the system to lubricate and/or cool the shaft 51'. Rotation of the proximal end of the shaft 51' by the motor 30a results in rotation of the entire length of the shaft 51' through the elongate body 20' and also results in rotation of the drive magnet 17. Rotation of the drive magnet 17 causes rotation of one or more magnets in the impeller 6 to create flow through the pump 2 by virtue of magnetic attraction of these magnets across the distal drive unit cover. In other embodiments, the shaft 51' can be directly mechanically coupled to the impeller 6 such that rotation does not depend on magnetic coupling. One or more shaft rotation supports 54A can be provided within a distal housing 29A to support a distal portion of the shaft 51'. The elongate body 20' and/or the shaft 51' can comprise a tether to control or to aid in control of the position of the pump, e.g., to counter thrust forces of the impeller 6 to reduce or minimize movement of the pump 2 in operation.

Additional details of the pump 2 and related components shown in FIGS. 1A-1H may be found throughout International Patent Application No. PCT/US2020/062928, filed on Dec. 2, 2020, the entire contents of which are incorporated by reference herein in their entirety and for all purposes.

II. Struts

As explained herein, the support structure or localization system 100 can comprise a plurality of struts 19. The struts 19 can have a first fixed end 38 at the base portion 36 that is coupled to or formed with the shroud 16, and a second free end 39 opposite the first end 38. The struts 19 can comprise projections extending from a housing (e.g., the pump housing 35) of a device, such as an intravascular device, extending radially and distally outwardly to make constant or intermittent contact with a vessel wall 37 (see FIGS. 4A-4B) of a vasculature system of a patient. As explained above, in other embodiments, the struts 19 may extend proximally relative to the pump housing 35 and/or the motor housing 29. As shown in, e.g., FIGS. 1A-1C, the struts 19 can extend distal the first fluid port 27 and the impeller 6 along the longitudinal axis L. In embodiments in which the vasculature is accessed through the femoral artery, the struts 19 can extend distally and upstream of the first fluid port 27 and the impeller 6. In embodiments in which the vasculature is accessed through the subclavian artery, the struts 19 can extend downstream of the fluid port 27. The struts 19 can extend to and at least partially define a distal-most end of the blood flow assist system 1. In some embodiments, no portion of the blood flow assist system 1 is disposed distal the distal end of the struts 19. In some embodiments, the struts 19 may be made of a flexible shape set metal or alloy like nitinol. A support structure 100 including a plurality of struts 19 may be used to provide localization of an intravascular device such as the pump 2. Using a plurality of struts 19 allows each of the struts 19, by acting in opposition to each other, to transmit a radial force to the region of the strut 19 in contact with the vessel wall 37. A plurality of struts 19 may also be effective in positioning an intravascular device (such as the pump 2) or part of an intravascular device relative to the vessel wall 37. For example, a plurality of struts 19 surrounding the first fluid port 27 (e.g., an inlet port in some embodiments) of the intravascular pump 2 effectively positions the inlet port 27 of the pump 2 at approximately the center of the blood vessel 37. Struts 19 for localizing and positioning intravascular devices may have a collapsed configuration for moving through the sheath 28 (see FIG. 1H) for deployment or retrieval and an expanded configuration for providing localization and positioning.

FIG. 2A is an image showing a front perspective view of the localization system 100A, according to one embodiment. FIG. 2B is a schematic side view of the localization system 100A of FIG. 2A. FIG. 2C is a schematic plan view of a laser cut pattern for the localization system 100A. FIG. 2D is a schematic side plan view of a strut 19A having a dome- or spherical-shaped contact pad 24A. Unless otherwise noted, the components of FIGS. 2A-2D may be the same as or generally similar to like-numbered components of FIGS. 1A-1H, with some reference numbers appended by the letter "A." As shown in, for example, FIGS. 2A-2D, each strut 19A can comprise an elongate slender body that extends between the first end 38 and the second end 39. Each strut 19A can comprise a material (e.g., a shape memory alloy) that is configured to store strain energy when a transverse compressive load is applied, e.g., compressively along the radial axis R. The stored strain energy can be employed to maintain localization and/or positioning relative to the vessel wall 37, as explained herein. For example, the stored strain energy can be result in radially outward forces being applied against the vessel wall 37. The radially outward forces can at least in part serve to localize, stabilize, and/or position the pump 2 relative to the vessel wall 37.

In some embodiments, a portion of the strut 19A that makes contact with the vessel wall 37 may have a desired shape that aids localization and/or positioning. In some embodiments, a portion of a strut 19A, such as its second end 39, may comprise a contact element 104 configured to be shaped as a generally flat contact pad 24A. In the illustrated embodiment, the contact pad 24A is shown as being generally circular or domed. Other shaped ends may be suitable, such as an oval end or the like. In some embodiments, shapes for the contact pad 24 that avoid sharp corners and/or edges may be preferred. When deployed, the contact pad 24A can be pressed against the wall 37 of the vessel with a radial force transmitted by the strut 19A. As the pad 24A presses against the vessel wall 37, the vessel wall 37 may "pillow" up around the edges of the pad 24A or the pad may form a depression in which it sits. The elongate struts can be configured to apply a load to the vessel wall 37 (e.g., an aortic wall) when deployed to locally radially expand vessel wall tissue against which the contact pad 24A is apposed. For example, the contact pad 24 can be resiliently deflectable toward and away from the longitudinal axis L of the pump housing 35. The contact pad 24 can have a free state being spaced away from the longitudinal axis L of the pump housing 35 by a distance greater than a half-width of a blood vessel 37 into which the pump housing 35 is to be deployed.

The contact pad 24 can apply sufficient force to a wall of the blood vessel 37 to depress or pillow a portion of the contact pad 24 into the wall. The contact pad 24 can be configured to engage without hooking the wall of the blood vessel 37 when applied. In some arrangements, the struts 19A can flex with vessel wall movement (e.g., with vessel wall expansion and contraction) such that the struts 19A can maintain contact with the vessel 37 even when the vessel 37 expands or contracts. This pillowing may enhance the ability of the strut 19A and pad 24A to localize the intravascular device (e.g., pump 2) by resisting sliding motion of the pad 24A. The amount that the pad 24A presses into the vessel wall 37 (and therefore the amount of pillowing) may be controlled by adjusting the radial force the strut 19A transmits to the contact pad 24A. The pad 24A may have holes or irregular edges to enhance the pillowing effect.

As shown in FIGS. 2E-2G, struts 19A' may include contact pads 24B having "slide runner" edges 66 that flare or bevel away from the vessel wall 37 so that sharp edges are not pressed into the vessel wall 37. As shown in FIGS. 2E-2G, the contact pads 24B can include a contact surface 67 that engages and depresses into the vessel wall 37, such that a surrounding portion of the wall 37 extends radially inward relative to at least a portion (e.g., the contact surface 67) of the contact pad 24B that engages the wall 37. The profile of the pad 24B in FIGS. 2E-2G including the edge 66, the contact surface 67, and the elongate member of the strut 19A can define a convex profile or shape. In the illustrated arrangement, the contact surface 67 can comprise a generally planar or flat shape, and the edge 66 can extend at an obtuse angle relative to the contact surface 67. In some embodiments, the contact surface 67 can comprise a curved surface, such as a convex spherical or domed surface. Such designs reduce or minimize the potential for traumatic injury to the vessel wall 37, are non-endothelializing, and may aid removal without damaging the vessel. With sufficient radial force and pillowing, such designs may provide stable localization of the strut contact pad 24A.

As shown in FIGS. 2A-2B, the struts 19A can comprise knees 102 that can serve to keep the strut 19A away from the inner wall of the sheath 28 when the plurality of struts 19A is collapsed within the sheath 28, as shown above in FIG. 1H. The sheath 28 can comprise an inflection in which the curvature of the radially-outward facing surface of the strut 19A changes. As shown in FIG. 2B, for example, the struts 19A can comprise a plurality of segments 103a-103d that are integrally formed and connected with one another. A first segment 103a can extend from the base portion 36A distally and radially outwardly by an angle A relative to the longitudinal axis L. A second segment 103b can extend distally and radially inwardly from the distal end of the first segment 103a by an angle B relative to the longitudinal axis L. A third segment 103c can extend distally and radially outwardly from the distal end of the second segment 103b by an angle C relative to the longitudinal axis L. A fourth segment 103d can extend distally and radially inwardly from the distal end of the third segment 103c by an angle D relative to the longitudinal axis L.

Thus, as shown in FIG. 2B, the struts 19A can have multiple changes in curvature and/or angles along the lengths of the struts 19A. In various embodiments, the angle A can be in a range of 30° to 70°, in a range of 40° to 60°, or in a range of 45° to 55° relative to the longitudinal axis L. The angle B can be in a range of 10° to 30°, in a range of 15° to 25°, or in a range of 18° to 24° relative to the longitudinal axis L. The angle C can be in a range of 20° to 60°, in a range of 30° to 50°, or in a range of 35° to 45° relative to the longitudinal axis L. The angle D can be in a range of 20° to 45°, or in a range of 25° to 35° relative to the longitudinal axis L. The base portion 36A can have a first height H1 in a range of 0.1" to 0.3". In the expanded configuration, the radial separation along the radial axis R between the ends of the struts 19A can have a second height H2 in a range of 1" to 2", or in a range of 1.2" to 1.6".

Beneficially, the use of multiple angles and curvatures for the struts 19A can enable the struts 19A to provide sufficient localization and support for the pump 2. Additionally or alternatively, the use of multiple angles and/or curvatures for the struts can adequately space parts of the struts, for example the free ends of the struts 19A, from the inner wall of the sheath 28. The spacing of the pads 24A from the inside wall of the sheath 28 can reduce friction and/or damage to the struts 19A and/or sheath 28 when the pump 2 is moved within and/or into and out of the sheath 28. Further, as explained above, the flat contact pads 24A can beneficially provide an atraumatic interface between the struts 19A and the vessel wall 37 that provides sufficient localization and/or positioning. The struts 19A can be manufactured by laser cutting a shape memory alloy as shown in, e.g., the laser cut pattern in a sheet of material of FIG. 2C. The shape memory alloy (e.g., nitinol) can be cut with a laser or other device and shaped to form the struts 19A. The patterned material can be folded and/or rolled into a closed generally cylindrical profile. In other embodiments, the pattern can be cut from an already-formed tube.

In some embodiments, such as that shown in FIG. 2D, the contact pad 24A or distal portion of the strut 19A may include a spherical or domed-shaped profile 42 that serves as the contact surface 67. As a nonlimiting example, the spherical profile 42 may be formed as a ball of plastic or other material formed on the portion of the strut 19A to contact the vessel wall 37. As shown in FIGS. 2B-2D, for example, the spherical profile 42 can be disposed on a radially-outer surface 43 of the strut 19A that is configured to face and engage with the vessel wall 37. A radially-inner wall 44 can be disposed radially opposite the radially-outer surface 43. In FIG. 2C, the struts 19A can be circumferentially spaced apart such that there is a respective gap 45 between adjacent side surfaces of adjacent struts 19A of the plurality of struts 19A. A spherical contact feature 24A can be beneficially atraumatic, and may provide good pillowing and resistance to translation. As shown the contact pad 24A can comprise a generally circular (or elliptical) pad in a profile view that has a diameter greater than a width of an immediately adjacent expanse of the corresponding elongate strut 19A. The contact pad 24A can comprise an elongate member and an enlarged blood vessel wall contact surface (e.g., surface 67 in FIGS. 2D-2G) disposed at the end of the elongate member. In various embodiments, the contact pad 24A can comprise a convex cross-sectional profile along the radially-outer surface 43 of the strut 19A that faces the vessel wall 37. For example, the contact pads 24A can comprise a convex profile in a cross-sectional plane disposed transverse to the longitudinal axis L of the pump housing 35. In some embodiments, the contact pads 24A can comprise smooth surfaces free of sharp edges or hooks. In some embodiments, each of the contact pads 24A can comprise one or more scalloped edges to allow tissue of the vessel wall 37 to be received therein.

In some embodiments, the localization system 100A may have the goal of resisting, but not eliminating, the translation or rotation of a device (such as the pump 2) relative to the vessel wall 37. As a nonlimiting example, some strut 19A and/or contact pad 24A designs may allow some small degree of rotation of the device within the vessel, even when deployed. However, such designs may also leverage other features discussed herein to further increase resistance to rotation during operation of the device, such as increase resistance resulting from propulsion.

Figure 3E:
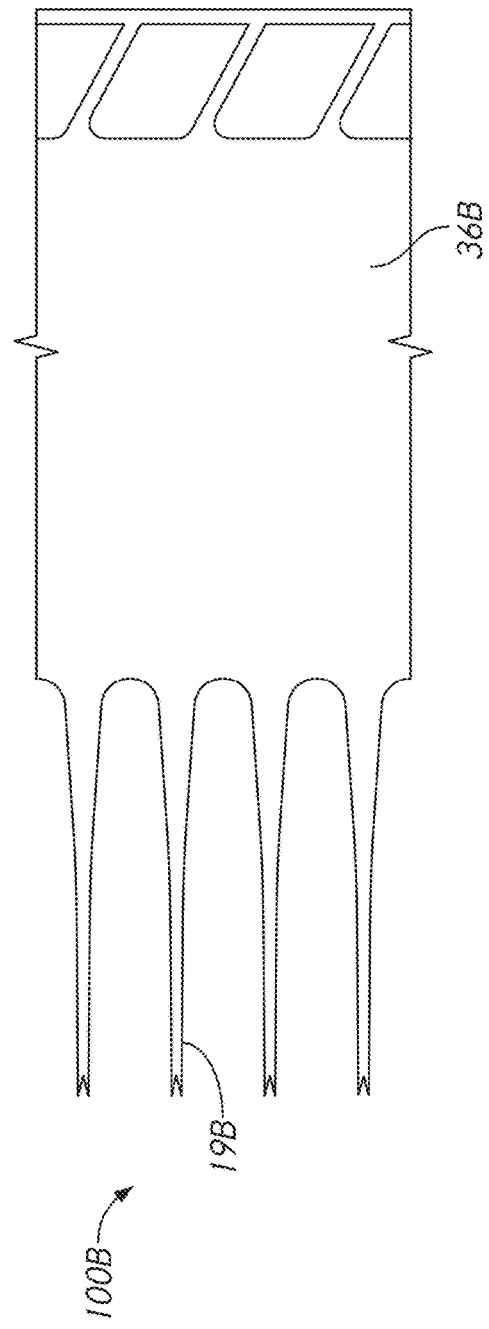
FIGS. 3E and 3F are schematic plan views of the localization system in a laser cut pattern prior to assembly.
Figure 3F:
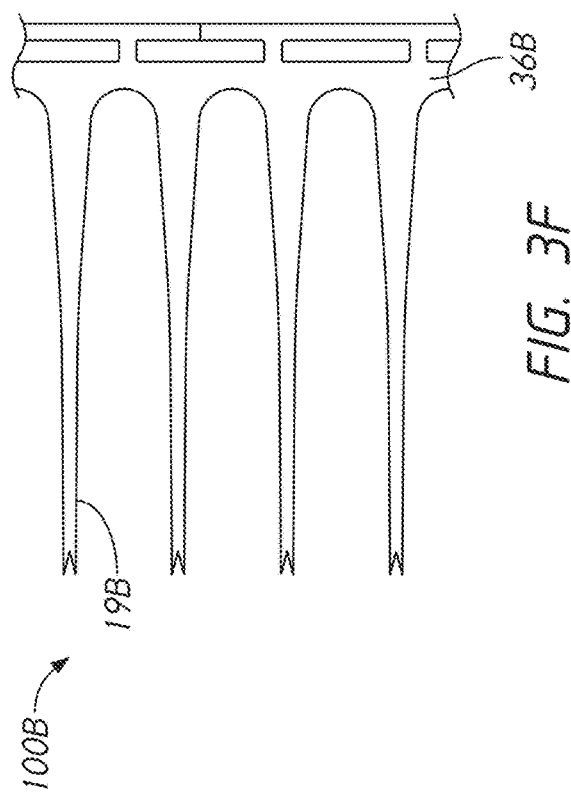

Alternatively, some embodiments of the contact pad may by designed to increase resistance to translation and/or rotation relative to the vessel wall 37. FIG. 3A is an image of a front perspective of a localization system 100B according to another embodiment. FIG. 3B is an image of a side view of the localization system 100B of FIG. 3A. FIG. 3C is a schematic side view of the localization system 100B of FIGS. 3A-3B. FIG. 3D is a schematic enlarged view of the second end 39 of the strut 19B of FIGS. 3A-3C. FIGS. 3E and 3F are schematic plan views of the localization system 100B in a laser cut pattern prior to assembly. Unless otherwise noted, the components of FIGS. 3A-3F may be the same as or generally similar to like-numbered components of FIGS. 1A-2C, with some reference numbers appended by the letter "B." In some embodiments, the contact element 104 (e.g., the portion of the strut 19B in contact with the wall 37 of the vessel) may comprise a hook 105 designed to penetrate the vessel wall 37 to provide a stable anchor point that has a high level or resistance to translation and/or rotation. Designs with edges or hooks 105 in constant contact with the vessel wall are typically intended to provide stable localization and/or positioning so there is little or no motion of the hook 105 or edge relative to the initial contact region of the vessel wall 37 when deployed.

As shown in FIG. 3C, the struts 19B can comprise a plurality of segments 106a-106d that are integrally formed and connected with one another. A first segment 106a can extend from the base portion 36B distally and radially outwardly by an angle E relative to the longitudinal axis L. A second segment 106b can extend distally and radially inwardly from the distal end of the first segment 106a so as to at least partially define an inflection point and/or knee 102 as explained above. A third segment 106c can extend distally and radially outwardly from the distal end of the second segment 106b by an angle F relative to the longitudinal axis L. A fourth segment 106d can extend back proximally from the distal end of the third segment 106c by an angle G relative to the third segment 106c. The third and fourth segments 106c, 106d can serve as the hook 105 and can secure the pump 2 to the vessel wall 37. As shown in FIG. 3G, which is a plan view of the fourth segment 106d, the fourth segment 106d of the strut 19B can include a split 106e having tines that can secure to a vessel wall, in some embodiments. As shown, in some embodiments, a tine width $t_w$ can be in a range of, e.g., 0.01" to 0.1", or in a range of 0.01" to 0.05".

As shown in FIG. 3C, the struts 19B can have multiple changes in curvature and/or angles along the lengths of the struts 19B. In various embodiments, the angle E can be in a range of 30° to 70°, in a range of 40° to 60°, or in a range of 45° to 55° relative to the longitudinal axis L. The angle F can be in a range of 20° to 60°, in a range of 30° to 50°, or in a range of 35° to 45° relative to the longitudinal axis L. The angle G can be in a range of 40° to 80°, in a range of 50° to 70°, or in a range of 55° to 65° relative to the segment 106c, angled proximally as shown. The base portion 36B can have a first height H1 in a range of 0.1" to 0.3". In the expanded configuration, the radial separation along the radial axis R between the ends of the struts 19B can have a second height H2 in a range of 1" to 2", or in a range of 1" to 1.4". Further, as shown in FIG. 3C, the knee 102 can have a bump height $h_b$ that indicates the amount of the bulge or bump defined by the knee 102. The bump height $h_b$ can be measured between an outwardly-facing crest of the knee 102 and a projection of the third segment 106c. In various embodiments, the bump height $h_b$ can be in a range of 0.03" to 0.09", or in a range of 0.05" to 0.07" (e.g., about 0.054" in one embodiment). In addition, the fourth segment 106d can serve as a tine of the hook 105 and can have a tine length $l_t$ extending proximally from the third segment 106c. The tine length $l_t$ can be in a range of 0.03" to 0.09", or in a range of 0.05" to 0.07" (e.g., about 0.058" in one embodiment).

FIGS. 3E-3F show laser patterns for the system 100B of FIGS. 3A-3D. As shown in FIGS. 3E-3F, in some embodiments, the struts 19B can be tapered across their width from proximal to distal along their length, i.e., from right to left in FIGS. 3E-3F. Laser cuts can be made non-normal to the longitudinal axis, which can create a helical or spiral pattern in various arrangements.

FIG. 5A is a schematic perspective view of a localization system 100C according to another embodiment. FIG. 5B is a schematic plan view of a laser cut design for the system 100C of FIG. 5A. Unless otherwise noted, the components of FIGS. 5A-5B may be the same as or generally similar to like-numbered components of FIGS. 1A-4E, with some reference numbers appended by the letter "C." In some embodiments, as shown in FIGS. 5A-5B, the plurality of struts 19C may differ in length. For example, as shown in FIGS. 5A-5B, the system 100C an include struts 19C arranged in a jester hat design. As shown, adjacent struts 19C may have different lengths. In some embodiments, every other strut may be designed to have approximately the same length. For example, as shown in FIGS. 5A-5B, first struts 19C' of the plurality of struts 19C may have a first length, and second struts 19C" of the plurality of struts 19C may have a second length 19C" shorter than the first length. The second struts 19C" may each be disposed circumferentially between the first struts 19C'. Although not illustrated in FIGS. 5A-5B, the struts 19C can include contact pads 24 at distal end portions thereof. In other embodiments, the struts 19C can include hooks 105 at distal end portions thereof.

Without being limited by theory, the different lengths may enable the system 100C to be supported against the vessel 37 at a plurality of longitudinal locations along the length of the vessel 37, which can improve localization and positioning. For example, in the expanded configuration of the struts 19C', 19C", the first struts 19C' can engage with the vessel wall 37 at a location distal the location at which the second struts 19C" engages with the vessel wall 37, such that the first and second struts 19C', 19C" engage with the vessel wall 37 at offset longitudinal positions. Engagement at offset longitudinal positions of the vessel wall 37 can beneficially improve stabilization of the pump 2 along multiple planes, and can also provide a resisting moment with multiple planes of contact. Moreover, the differing lengths of the struts 19C', 19C" can improve collapsibility of the struts by allowing the sheath 28 to separately engage the struts 19C' and 19C". For example, due to the differing lengths (and/or curvature) of the struts 19C', 19C", the sheath 28 may first engage a first set of struts (e.g., struts 19C" in some embodiments) to cause the first set of struts to begin collapsing. During or after collapse of the first set of struts, the sheath 28 may subsequently engage a second set of struts (e.g., struts 19C' in some embodiments) to cause the second set of struts to collapse. Dividing the collapse of the struts 19C', 19C" into two or more stages can beneficially reduce the amount of force used to collapse the respective struts 19C', 19C".

It should be appreciated that any of the support structures disclosed herein can comprise struts having different lengths. For example, in some embodiments, the plurality of struts (e.g., struts 19 or 19A) includes a first plurality of struts and a second plurality of struts. When the plurality of struts are in an expanded configuration, first contact elements (e.g., contact pads 24 or hooks 105) of the first plurality of struts can be configured to engage with the blood vessel wall at a first longitudinal position and second contact elements (e.g., contact pads 24 or hooks 105) of the second plurality of struts can be configured to engage with the blood vessel wall at a second longitudinal position that is spaced from the first longitudinal position. In some embodiments, the struts in the first plurality can have a different length from the struts in the second plurality. Additionally or alternatively, the struts in the first plurality can have a different radius of curvature (or departure angle) from the struts in the second plurality.

FIG. 6 is a schematic side view of a plurality of struts 19D according to various embodiments. In some embodiments, as shown in FIG. 6, a first set of struts 19D' may have an elongate portion with a first radius of curvature, and a second set of struts 19D" may have an elongate portion with a second radius of curvature different than (e.g., less than) the first. In the arrangement of FIG. 6, the first struts 19D' have a steeper takeoff angle relative to the longitudinal axis L as compared with the second struts 19D". An angle between a longitudinal axis of the pump 2 and of a portion of the second struts 19D" adjacent to a base portion to which the struts are connected can be greater than a corresponding angle for the first struts 19D', as shown in FIG. 6. The steeper takeoff angle of the first struts 19D' may cause the sheath 28 to engage with and initiate collapse of the first struts 19D' before engagement with the second struts 19D". As explained above, staging, staggering or sequencing the collapse of the struts 19D', 19D" can beneficially reduce the force used to collapse the struts so as to improve operation of the pump 2. Staging, staggering, or sequencing the collapse of the struts can modulate the force profile over the length of motion of the sheath 28 over the struts 19 as felt from initial movement prior to collapsing, to the initial collapsing adjacent to the base 36, to final and full collapsing of the struts 19 by advancing the sheath adjacent to or beyond the distal ends of the struts. Staging, staggering, or sequencing can reduce the maximum force required over the length of motion of the sheath 28 over the struts 19. Moreover, the different curvature of the struts 19D', 19D" may also allow the distal ends of the struts 19D', 19D" to engage the vessel wall 37 at offset longitudinal positions, which, as explained above, can improve stabilization of the pump 2 due to, e.g., multiple planes or rings of contact with the vessel wall 37.

FIG. 6 thus illustrates embodiments where the struts 19D', 19D" may have approximately the same length along the longitudinal direction from proximal to distal ends in the retracted state but which may expand to contact a vessel wall at offset longitudinal positions, e.g., as may be defined by two spaced apart planes disposed transverse to, e.g., perpendicular to the longitudinal axis of the pump 2. The struts 19D', 19D", individually or in groups defining contact planes, can at least intermittently contact the vessel wall over a range of positions along the vessel wall that is two times, three times, four times, five times, six times, up to ten time, or up to one hundred times greater than the contact length of a contact pad or other vessel wall contact surface of the struts. It will be appreciated that dispersed contact areas of these sorts can also be provided by struts that have different lengths in the retracted state, as in FIGS. 5A-5B. In some embodiments, the contact element 104 at the second free end 39 of a strut 19D may be curled or coiled so that curled portion will contact the vessel wall 37. As a nonlimiting example, the second free end 39 of the strut 39D may be curled or coiled (e.g., at an angle in a range of approximately 270° to) 360°.

The contact area of the contact element 104 of a strut 19-19D may be designed so that endothelialization over longer durations does not impede or prevent removal of the device or increase the potential for trauma to the vessel wall 37 when the intravascular device (e.g., pump 2) is removed. In general, single-ended contact geometries can be pulled out more easily from under any endothelialization. In contrast, non-single ended contact geometries may increase the potential for trauma to the vessel wall 37 when the device is removed. In some embodiments with hooks 105, the strut 19B can be shaped so the action of advancing the sheath 28 to collapse the plurality of struts 19B will move the struts 19B in such a way as to pull the hooks 105 from the vessel wall 37 like a dart from a dartboard or in the opposite direction from which it was inserted. In some embodiments with contact pads 24, 24A, the pads 24, 24A may be tapered so they can be pulled out from under endothelialized tissue by translating the intravascular device (e.g., pump 2). Raising the edges of the contact pad 24, 24A (e.g., a "sled"-type design) may also discourage restrictive endothelialization.

The amount of radial force that presses the contact area at the second free end 39 of a strut 19-19D against the blood vessel wall 37 can be altered by varying the number of struts 19-19D, material of the struts 19-19D, and/or the geometry of the struts 19-19D and contact pads 24-24A. Important geometric factors may include, but are not limited to, the length of the strut 19-19D, cross-section of the strut 19-19D, attachment angle of the strut 19-19D to the pump housing 35, and curvature of the strut 19-19D. In general, a strut 19-19D will have a spring function, such that the more the strut 19-19D is compressed by the vessel wall 37, the higher the radial force of the strut 19-19D on the vessel wall 37. The design and shape forming of the strut may be selected to reduce this dependence so that the radial force provided by the strut 19-19D is relatively independent of the radius to which the strut is compressed. Equalization of such spring forces among a plurality of struts 19-19D can provide a centering positioning effect.

In some embodiments, a strut 19-19D may be designed for intermittent contact and have zero radial force unless it is in contact with the vessel wall 37. As a nonlimiting example, the plurality of struts 19-19D may have different lengths and/or geometries (e.g., FIGS. 5A-5B). The different lengths and/or geometries may arrange the struts 19C so that not all struts 19C touch the vessel wall 37 at the same time in some embodiments as shown in FIGS. 5A-5B. Further, is some example the struts 19-19D may be utilized with devices that exert forces on the struts 19-19D during operation (e.g., a gyroscopic effect), which may result in changes in forces exerted on the struts 19-19D. Because of the spring-like nature of the struts 19-19D, collapse or release in such situations can be facilitated. Note that each strut 19-19D in a plurality of struts may have a different geometry or contact region design.

In some embodiments, the struts 19-19D can have knees 102 as explained above. A knee 102 in a strut may function to keep part of the strut 19A-19D away from the inner wall of the sheath 28 when the plurality of struts 19A-19D are collapsed within the sheath 28. For example, the knee 102 may function to keep a hook 105 away from the inner wall of the sheath 28 so that the hook 105 does not contact the sheath 28 and create particulates through abrasion, cutting, or gouging. The knee 102 can comprise an inflection zone disposed between the first end 38 and the second end 39, the second end 39 resiliently deflectable toward and away from the longitudinal axis L of the pump housing 35. A free state of the strut can space the second end 39 thereof away from the longitudinal axis L of the pump housing 35. The second end 39 of the strut can be configured to engage the blood vessel wall 37 (e.g., to at least intermittently contact the vessel wall 37). The inflection zone can comprise an S-connection between a first span of the strut and a second span of the strut. The first span and the second span can be disposed along parallel trajectories.

Minimizing the diameter of the sheath 28 used to implant or retrieve an intravascular device (such as the pump 2) can be important. An advantage of the embodiments disclosed herein is that the plurality of struts 19-19D can be collapsed to a diameter equal to or smaller than the diameter of the pump 2 itself so that a large sheath is not required due to the presence of the plurality of struts 19-19D.

In some embodiments, a plurality of struts 19-19D may be designed to contact the vessel wall 37 in multiple transverse planes (for example, at multiple longitudinal positions) along the central axis of the vessel. In some embodiments, a plurality of struts 19-19D may be attached to the pump 2 in one transverse plane, but the struts 19-19D can have different geometries and can contact the vessel wall 37 in multiple transverse planes along the central axis of the vessel. In some embodiments the plurality of struts 19-19D may be attached to the pump 2 in more than one transverse plane along the central or longitudinal axis L of the pump 2. As a nonlimiting example, there may be a set of struts 19-19D at each end of the pump 2 (e.g., at proximal and distal ends of the pump 2).

In some embodiments, a plurality of struts 19-19D may be directly integrated into the pump 2 such that the shroud 16 and struts 19-19D are monolithically formed in a single piece. In other embodiments, the plurality of struts 19-19D may be coupled or connected to the pump 2 instead and may comprise one or more separate piece(s). As a nonlimiting example, the struts 19-19D may be attached a ring that is attached to the pump 2.

Tether

In some embodiments, one or more tethers may be a component of the localization and positioning system 100-100C. Devices, such as the pump 2, that utilize a cable or lead for power or infusion can use that cable or lead as a tether. For example, as shown herein, the power lead 20 can serves as the tether in the illustrated embodiments. The tether (e.g., power lead 20) can have an anchor point outside the blood vessel and/or the patient, and can limit translation of the intravascular device (e.g. away from that anchor point). As explained herein, for example, the connector 23 at the proximal end 21 of the system 1 can connect to a console (which can serve as the anchor point in some embodiments) outside of the patient's body. In some embodiments, the arteriotomy and path through the skin of the patient can serve as the anchor point for the tether. Sutures may be used to anchor the tether (e.g., power lead 20) adjacent to the proximal end 21 in some procedures.

Propulsion

Figure 4A:
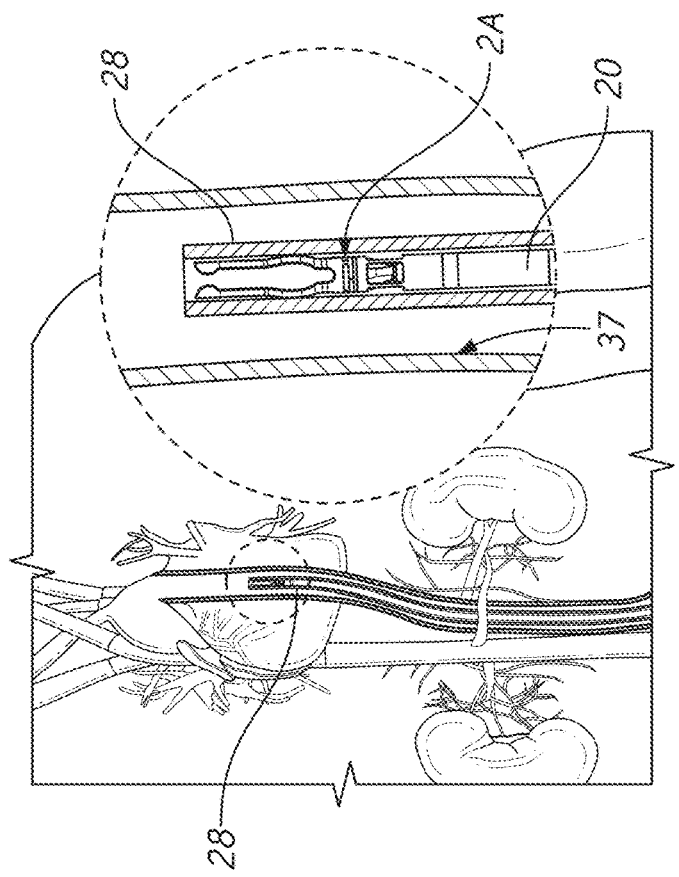
Figure 4B:
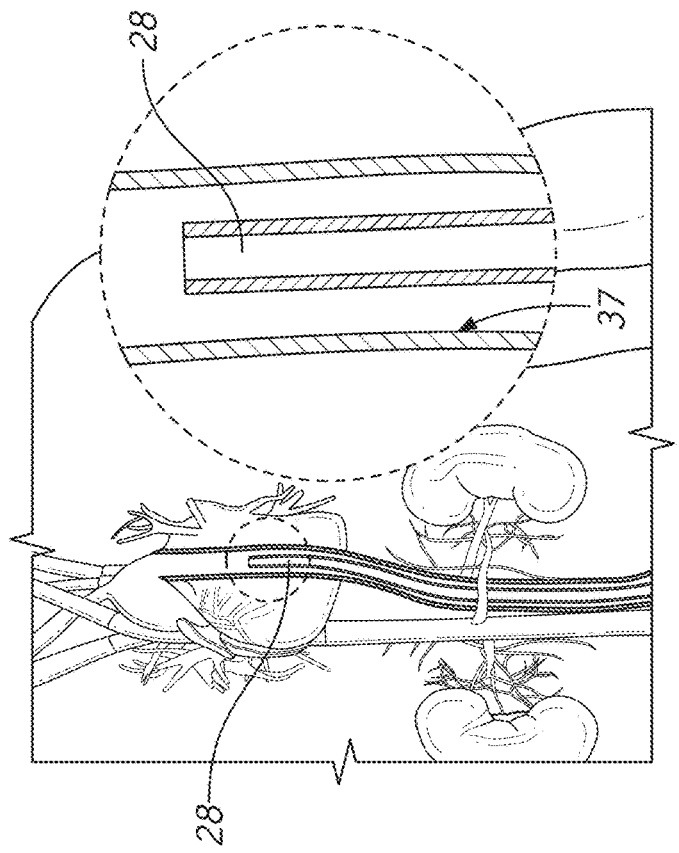

One nonlimiting example of intravascular devices that may be used with the disclosed embodiments is the blood pump 2A, as shown in, e.g., FIGS. 4A-4E. As shown in FIG. 4A, and as explained above, the sheath 28 can be inserted percutaneously to a treatment location in a blood vessel, such as the descending aorta. In some embodiments, as shown in FIG. 4B, after placement of the sheath 28, the pump 2A can be pushed distally within the sheath 28 by way of a stiffening member or guidewire (not shown) that can be disposed within the central lumen 55. In other embodiments, the pump 2A can be pre-loaded in the sheath 28, and the sheath 28 and pump 2A can be advanced together to the treatment location. As shown in FIGS. 4C-4D, relative motion can be provided between the sheath 28 and the pump 2A to urge the pump 2A out of the sheath 28. The support structure including the struts 19-19D can self-expand and contact the inner wall of the vessel 37. The struts used in the support structure of the pump 2A shown in FIGS. 4A-4E can include any of the struts 19-19D described herein. For example, in some embodiments, such as that shown in FIG. 4C, a mesh 47 can extend or span between adjacent struts at a location near the distal end of the shroud 16. The mesh 47 can extend partially along length(s) of the struts, e.g., within a range of 10% to 70% of a length of the strut(s). The struts 19A of FIG. 4D are shown with the contact pads 24. The struts of FIG. 4E are shown with the hooks 105.

Once the struts are deployed, the impeller 6 can be activated to pump blood. Some blood pumps 2A discharge blood in jets 34 or exert significant forces during operation. These pumps 2A may generate a reaction (or propulsive) force 33 on the pump 2A in the opposite direction of the pump discharge, e.g. when pumping down a propulsive force 33 may result upwardly as shown in FIG. 4D. Some embodiments may be designed to take advantage of this propulsive force 33 as a component of the localization system 100-100C. As a nonlimiting example, the struts 19-19D may provide a geometry that causes an increase in the spring-like forces as a result of the propulsive force 33, e.g., the propulsive force 33 may further compress the struts 19-19D and increase the spring force. In various embodiments, a longitudinal component of the thrust force 33 along the longitudinal axis L can be opposed by tension in the tether (e.g., the power lead 20). A transverse component of the thrust force 33 directed transverse to the longitudinal axis L (e.g., along the radial axis R) can be opposed by strain energy stored in at least one of the elongate struts 19-19D upon deflection of the strut(s) 19-19D. As explained herein, when the procedure is complete, the clinician can provide further relative motion between the sheath 28 and the pump 2A to collapse the struts 19-19D into the sheath 28 (see FIG. 1H).

Beneficially, in various embodiments disclosed herein, the power lead 20 can serve as a tether that is sufficiently strong so as to oppose loads applied in opposite directions at opposite ends thereof. In some pumps, the thrust from the pump 2 may be too strong such that, if the proximal end of the tether is not sufficiently anchored and/or if the power lead 20 is not sufficiently strong, the pump 2 can move through the blood vessel. In such a situation, the pump 2 may stretch the tether, and/or the tether may not be sufficiently anchored. Beneficially, the embodiments disclosed herein can utilize the elongate hollow member and conductor wires which can be sufficiently strong such that, when anchored outside the blood vessel, a longitudinal component of the thrust force generated by the impeller directed along the longitudinal axis of the pump can be adequately opposed by the tether. Thus, in various embodiments, the tether (e.g., power lead 20) can be configured to maintain a position of the pump 2 within the blood vessel without requiring contact between the pump 2 and a blood vessel wall 37 of the blood vessel.

In some embodiments, the struts of the support structure need not contact the wall 37 during operation of the blood pump 2, and the tether can serve to adequately position the pump 2. In some procedures, the strut(s) may at least intermittently contact the blood vessel wall 37 (e.g., the struts may only intermittently contact the wall 37). In such arrangements, the strut(s) may intermittently come into contact with the wall 37 and move away from the vessel wall 37 throughout the procedure. Accordingly, the embodiments disclosed herein need not require constant contact between the support structure of the pump and the vessel wall 37. Indeed, in such embodiments, the struts may comprise short and/or stubby struts that may serve as bumpers that atraumatically, e.g., resiliently, engage with the vessel wall 37 intermittently as the pump 2 moves towards the wall 37, and pushes the pump 2 back towards a central location of the vessel. In some embodiments, the struts may be omitted such that the tether and thrust force establish the position of the pump in operation. In other embodiments, however, the struts may be shaped or configured to maintain substantially constant contact with the vessel wall 37 when in the deployed configuration during use of the pump 2. In still other embodiments, the pump 2 may not include struts, such that the tether may serve the positioning and/or localization function without struts.

Example Designs

The various design features discussed above may be mixed and combined in any fashion desired. Nonlimiting examples described herein below illustrate one possible embodiment that combines the design elements described above and are not an indication of the bounds of potential combinations.

The systems and methods discussed herein are used to provide localization and positioning of a device, such as an intravascular pump 2, 2A. A plurality of struts 19-19D with contact elements 104 project out from a ring attached to the inlet end of the pump 2. The embodiments of FIGS. 1A-3G show four struts 19-19B, but any number of struts may be used. For example, as shown in FIGS. 5A-5B, in some embodiments more than four struts (e.g., six struts 19C) can be used. The contact pads 24, 24A are shown as circular, but any shaped contact pads 24, 24A may be used. The strut geometry is designed to provide radial force within a set range at the strut contact pads 24, 24A for vessels within a certain diameter range. The struts 19-19D can also be designed to reduce or minimize the force required for the sheath 28 to collapse the struts 19-19D.

The circular contact pads 24, 24A can be designed to slide on the inner artery wall 37 rather than cause any trauma. With this tuning of the radial force, the plurality of expanded struts 19-19D provides consistent positioning of the inlet port 27-27B of the pump 2, 2a in the center of the vessel lumen and resists, but does not strictly prevent, translation and rotation of the pump 2, 2a. This feature allows safe translation of the pump 2, 2a whether intentional (to move the pump 2, 2A to a preferred location) or unintentional (e.g., if the power lead is yanked).

Providing limited localization is sufficient because in some embodiments the propulsive force 33 of the pump 2, 2A tends to move it in a superior direction, and/or this movement may be limited by the tether effect of the pump's power lead 20. One advantage of this embodiment is providing stable long-term localization, while allowing instantaneous movement of the pump 2, 2A with minimal or reduced risk of trauma to the vessel wall 37. This embodiment, for example, is compatible with a greater freedom-of-motion for the patient who is free to sit up, bend at the waist, and/or make other similar motions.

In some embodiments, the strut geometry may be altered so that the struts 19-19D only make intermittent contact with the vessel wall 37. In such an embodiment, the propulsive force 33 acting against the tether (e.g., power lead 20) provides localization and the struts 19-19D maintain positioning of the port 27-27B of the pump 2, 2A in the center of the lumen of the vessel.

Advantages

The systems and methods discussed herein, including without limitation the embodiment described in detail and illustrated in the drawings, has a number of advantages. Many of these advantages are described above. The following are only additional non-limiting examples of advantages, some of which arise from the combination of various design elements.

a. Struts 19-19D (including struts 19C', 19C", 19D', 19D") designed to not increase the diameter of the pump 2 when the struts 19-19D are in the collapsed configuration.

b. Struts 19-19D (including struts 19C', 19C", 19D', 19D") with knees 102 and hooks 105, such that the knees 102 prevent the hooks 105 from contacting the inner surface of the sheath 28 during implantation or retrieval of the pump 2.

c. Atraumatic contact pads 24, 24A designed to resist, but not eliminate translation or rotation of the intravascular device (e.g., pump 2, 2A) that
  i. Work in conjunction with a tether (e.g., power lead 20) and propulsive force 33; and/or
  ii. Become more resistant to translation over time due to desired endothelialization.

d. Intermittent contact positioning (centering) with struts 19-19D (including struts 19C', 19C", 19D', 19D") with long-term localization effected by the propulsive force 33 working against a tether (e.g., power lead 20).

Embodiments described herein are included to demonstrate particular aspects of the present disclosure. It should be appreciated by those of ordinary skill in the art that the embodiments described herein merely represent exemplary embodiments (e.g., non-limiting examples) of the disclosure. Those of ordinary skill in the art should, in light of the present disclosure, appreciate that many changes can be made in the specific embodiments described, including various combinations of the different elements, components, steps, features, or the like of the embodiments described, and still obtain a like or similar result without departing from the spirit and scope of the present disclosure. From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure.

Prior work is detailed in U.S. Pat. No. 8,012,079 and U.S. Pat. Pub. No. 2017/0087288, which are both fully incorporated by reference herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted fairly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A method of operating a blood flow assist system, the method comprising: deploying a pump at a treatment location within a blood vessel of a patient, the pump including an impeller and a tether extending proximally from the impeller, the tether configured to oppose loads applied in opposite directions at opposite ends thereof; and rotating the impeller to pump blood and to generate a thrust force, wherein a longitudinal component of the thrust force generated by the impeller directed along a longitudinal axis of the pump is opposed by the tether, the tether configured to maintain a position of the pump within the blood vessel without requiring contact between the pump and a blood vessel wall of the blood vessel.

2. The method of claim 1, wherein the pump comprises a pump housing, the impeller disposed in the pump housing, wherein the pump includes a plurality of elongate struts extending distally from the pump housing in a collapsed configuration.

3. The method of claim 2, further comprising removing the pump from a sheath.

4. The method of claim 3, wherein removing the pump from the sheath comprises expanding the plurality of elongate struts from the collapsed configuration to an expanded configuration.

5. The method of claim 4, wherein expanding the plurality of elongate struts comprises causing the plurality of elongate struts to radially self-expand to the expanded configuration in which at least one strut makes at least intermittent contact with the blood vessel wall of the blood vessel to maintain spacing of the pump from the blood vessel wall.

6. The method of claim 5, wherein each elongate strut of the plurality of elongate struts includes a convex contact pad at a distal end thereof.

7. The method of claim 6, further comprising causing the convex contact pad of the at least one strut to make only intermittent contact with the blood vessel wall of the blood vessel.

8. The method of claim 6, further comprising causing a portion of the convex contact pad to depress into the vessel wall.

9. The method of claim 2, wherein each elongate strut of the plurality of elongate struts includes an inflection zone disposed between a distal end and a proximal end of the elongate strut.

10. The method of claim 9, wherein the inflection zone of each strut spaces the distal end of the strut from an inner wall of a sheath within which the struts are disposed in the collapsed configuration.

11. The method of claim 1, wherein rotating the impeller comprises conveying electrical current to a motor by way of the tether which comprises a conductor, the motor operatively coupled with the impeller.

12. The method of claim 4, further comprising collapsing the plurality of elongate struts.

13. The method of claim 12, wherein each strut of the plurality of elongate struts comprises a knee, wherein collapsing the plurality of elongate struts comprises engaging each knee with a distal end of the sheath.

14. The method of claim 12, further comprising, after the collapsing, removing the pump from the patient.

* * * * *